US012741234B2

(12) United States Patent
Marcus et al.

(10) Patent No.: US 12,741,234 B2
(45) **Date of Patent: *Sep. 22, 2026**

(54) CHANNELED FIBERS IN SEPARATION OF BIOLOGICALLY ACTIVE NANOPARTICLES

(71) Applicant: CLEMSON UNIVERSITY RESEARCH FOUNDATION, Clemson, SC (US)

(72) Inventors: R. Kenneth Marcus, Clemson, SC (US); Terri F. Bruce, Clemson, SC (US); Lei Wang, Clemson, SC (US); Sisi Huang, Clemson, SC (US); Tyler Y. Slonecki, Clemson, SC (US); Rhonda Reigers Powell, Clemson, SC (US)

(73) Assignee: CLEMSON UNIVERSITY RESEARCH FOUNDATION, Clemson, SC (US)

( * ) Notice: Subject to any disclaimer, the term of this patent is extended or adjusted under 35 U.S.C. 154(b) by 529 days.

This patent is subject to a terminal disclaimer.

(21) Appl. No.: 18/108,828

(22) Filed: Feb. 13, 2023

(65) Prior Publication Data

US 2023/0191283 A1 Jun. 22, 2023

Related U.S. Application Data

(63) Continuation of application No. 16/267,579, filed on Feb. 5, 2019, now Pat. No. 11,596,876.

(60) Provisional application No. 62/626,398, filed on Feb. 5, 2018.

(51) Int. Cl.

| | |
|---|---|
| ***B01D 15/32*** | (2006.01) |
| ***C07K 14/47*** | (2006.01) |
| ***C12N 9/00*** | (2006.01) |
| ***C12N 15/10*** | (2006.01) |
| ***G01N 1/40*** | (2006.01) |
| ***G01N 33/50*** | (2006.01) |
| *A61K 35/68* | (2006.01) |
| *B01J 20/26* | (2006.01) |
| *B01J 20/28* | (2006.01) |
| *B01J 20/285* | (2006.01) |
| *B01J 20/286* | (2006.01) |

(52) U.S. Cl.

CPC ............ *B01D 15/327* (2013.01); *C07K 14/47* (2013.01); *C12N 9/00* (2013.01); *C12N 15/10* (2013.01); *C12N 15/1017* (2013.01); *G01N 1/405* (2013.01); *G01N 33/5005* (2013.01); *A61K 35/68* (2013.01); *B01J 20/262* (2013.01); *B01J 20/28023* (2013.01); *B01J 20/285* (2013.01); *B01J 20/286* (2013.01); *B01J 2220/54* (2013.01)

(58) Field of Classification Search

CPC .. B01D 15/327; G01N 1/405; G01N 33/5005; B01J 20/285; B01J 20/28023; B01J 20/286; B01J 2220/54; C07K 14/47; C12N 15/10

See application file for complete search history.

(56) References Cited

U.S. PATENT DOCUMENTS

| | | | |
|---|---|---|---|
| 6,388,746 | B1 | 5/2002 | Eriksson et al. |
| 6,953,686 | B1 | 10/2005 | Ramasubramanyan et al. |
| 7,261,813 | B2 | 8/2007 | Marcus et al. |
| 7,740,763 | B2 | 6/2010 | Marcus et al. |
| 8,298,657 | B2 | 10/2012 | Bonner et al. |
| 8,901,284 | B2 | 12/2014 | Vlassov et al. |
| 9,081,012 | B2 | 7/2015 | Park et al. |
| 9,347,087 | B2 | 5/2016 | Vlassov et al. |
| 9,410,873 | B2 | 8/2016 | Wilson et al. |
| 2006/0032816 | A1 | 2/2006 | Marcus |
| 2006/0247361 | A1 | 11/2006 | Shah |
| 2008/0299671 | A1 | 12/2008 | Glad et al. |
| 2009/0047734 | A1 | 2/2009 | Berg et al. |
| 2015/0024511 | A1 | 1/2015 | Marcus et al. |
| 2015/0209299 | A1 | 7/2015 | Xia et al. |
| 2016/0266097 | A1 | 9/2016 | Gagnon |
| 2016/0266134 | A1 | 9/2016 | Marcus et al. |
| 2016/0274010 | A1 | 9/2016 | Ichiki et al. |
| 2017/0296626 | A1 | 10/2017 | Tarnopolsky |

FOREIGN PATENT DOCUMENTS

| | | |
|---|---|---|
| CA | 2049876 | 8/1991 |
| CN | 104634750 | 5/2015 |
| WO | WO 09/112949 | 9/1991 |
| WO | WO 2009/030944 | 3/2009 |
| WO | WO 2011/058439 | 5/2011 |

(Continued)

OTHER PUBLICATIONS

Adams, A. "Concentration of Epstein-Barr Virus from Cell Culture Fluids with Polyethylene Glycol" *J. Gen. Viral.* 20 (1973) pp. 391-394.

Boring et al. "Single-step isolation of extracellular vesicles by size-exclusion chromatography". Journal of Extracellular Vesicles by size-exclusion chromatography. Journal of Extracellular Vesicles 2014, 3:23430, pp. 1-11. (Year: 2014).

Cohen, et al. "A capillary-scale liquid chromatography system that improves the practical sensitivity of HPLC-MS(MS) analysis" *American Laboratory* (1999) pp. 28-32.

Freemantle, M. "Downsizing Chemistry: Chemical analysis and synthesis on microchips promise a variety of potential benefits" *Chem. Eng. News* 77(8) (1999) pp. 27-36.

(Continued)

*Primary Examiner* — Shafiqul Haq

(74) *Attorney, Agent, or Firm* — Dority & Manning, P.A.

(57) ABSTRACT

A relatively fast, inexpensive, and non-destructive method for separation and isolation of biologically active nanoparticles is described. Methods include the use of solid phase separation medis such as channeled fibers in a hydrophobic interaction chromatography (HIC) protocol to isolate biologically active nanoparticles from other components of a mixture. Biologically active nanoparticles can include natural nanoparticles (e.g., exosomes, lysosomes, virus particles) as well as synthetic nanoparticles (liposomes, genetically modified virus particles, etc.)

22 Claims, 17 Drawing Sheets

(56) References Cited

FOREIGN PATENT DOCUMENTS

| | | |
|---|---|---|
| WO | WO 2016/093926 | 6/2016 |
| WO | WO 2017/223048 | 12/2017 |

OTHER PUBLICATIONS

Jiang, et al. "Polyethylenimine modified poly(ethylene terephthalate) capillary channeled-polymer fibers for anion exchange chromatography of proteins" *Journal of Chromatography A* 1410 (2015) pp. 200-209.

Kandel, et al. "Incorporating functionalized polyethylene glycol lipids into reprecipitated conjugated polymer nanoparticles for bioconjugation and targeted labeling of cells" *Nanoscale* 3(3) (2011) pp. 1037-1045.

Keller et al. "Body Fluid Derived Exosomes as a Novel Template for Clinical Diagnostics". Journal of Translational Medicine 2011, vol. 9, Issue 86, pp. 1-9. (Year: 2011).

Lewis, et al. "Polyethylene Glycol Precipitation for Recovery of Pathogenic Viruses, Including Hepatitis A Virus and Human Rotavirus, from Oyster, Water, and Sediment Samples" *Applied and Environmental Microbiology* 54(8) (1988) pp. 1983-1988.

Majors, et al. "Micropipette Tip-Based Sample Preparation for Bioanalysis" *Advanstar Communications, Inc*. (2005) pp. 1-6.

Marcus, et al. "Capillary-channeled polymer fibers as stationary phases in liquid chromatography separations" *J. Chromatogr. A* 986 (2003) pp. 17-31.

Momen-Heravi, et al. "Current methods for the isolation of extracellular Vesicles" *Biol. Chem*. 394(10) (2013) pp. 1253-1262.

Nelson, et al. "A Novel Stationary Phase: Capillary-Channeled Polymer (C-CP) Fibers for HPLC Separations of Proteins" *Journal of Chromatographic Science* 41 (2003) pp. 475-479.

Pocsfalvi, et al. "Chromatography and its hyphenation to mass spectrometry for extracellular vesicle analysis" *Journal of Chromatography A* 1439 (2016) pp. 26-41.

Schadock-Hewitt, et al. "Loading characteristics and chemical stability of headgroup-functionalized poly(ethylene glycol)-lipid ligand tethers on polypropylene capillary-channeled polymer fibers" *J. Sep. Sci*. 37 (2014) pp. 3595-3602.

Schadock-Hewitt, et al. "Head group-functionalized poly(ethyleneglycol)-lipid (PEG-lipid) surface modification for highly selective analyte extractions on capillary-channeled polymer (C-CP) fibers" *Analyst* 139 (2014) pp. 2108-2113.

Schmitt, et al. "Synthesis and Characterization of Chelator-Lipids for Reversible Immobilization of Engineered Proteins at Self-Assembled Lipid Interfaces" *J. Am. Chem. Soc*. 116 (1994) pp. 8485-8491.

Wang, et al. "Export of microRNAs and microRNA-protective protein by mammalian cells" *Nucleic Acids Res*. 38(2) (2010) pp. 7248-7259.

Stranska, et al. "Comparison of membrane affinity-based method with size-exclusion chromatography for isolation of exosome-like vesicles from human plasma" *J. Transl. Med*. 16(1) (2018) pp. 1-9.

Yamamoto, et al. "Rapid bacteriophage sedimentation in the presence of polyethylene glycol and its application to large-scale virus purification" *Virology* 40 (1970) pp. 734-744. (Abstract only).

Zeringer, et al. "Strategies for Isolation of Exosomes" *Cold Spring Harb Protoc* (2015) pp. 319-323.

Zhang, et al. "Parallel, open-channel lateral flow (immuno) assay substrate based on capillary-channeled polymer films" *Analyst* 141(3) (2016) pp. 807-814.

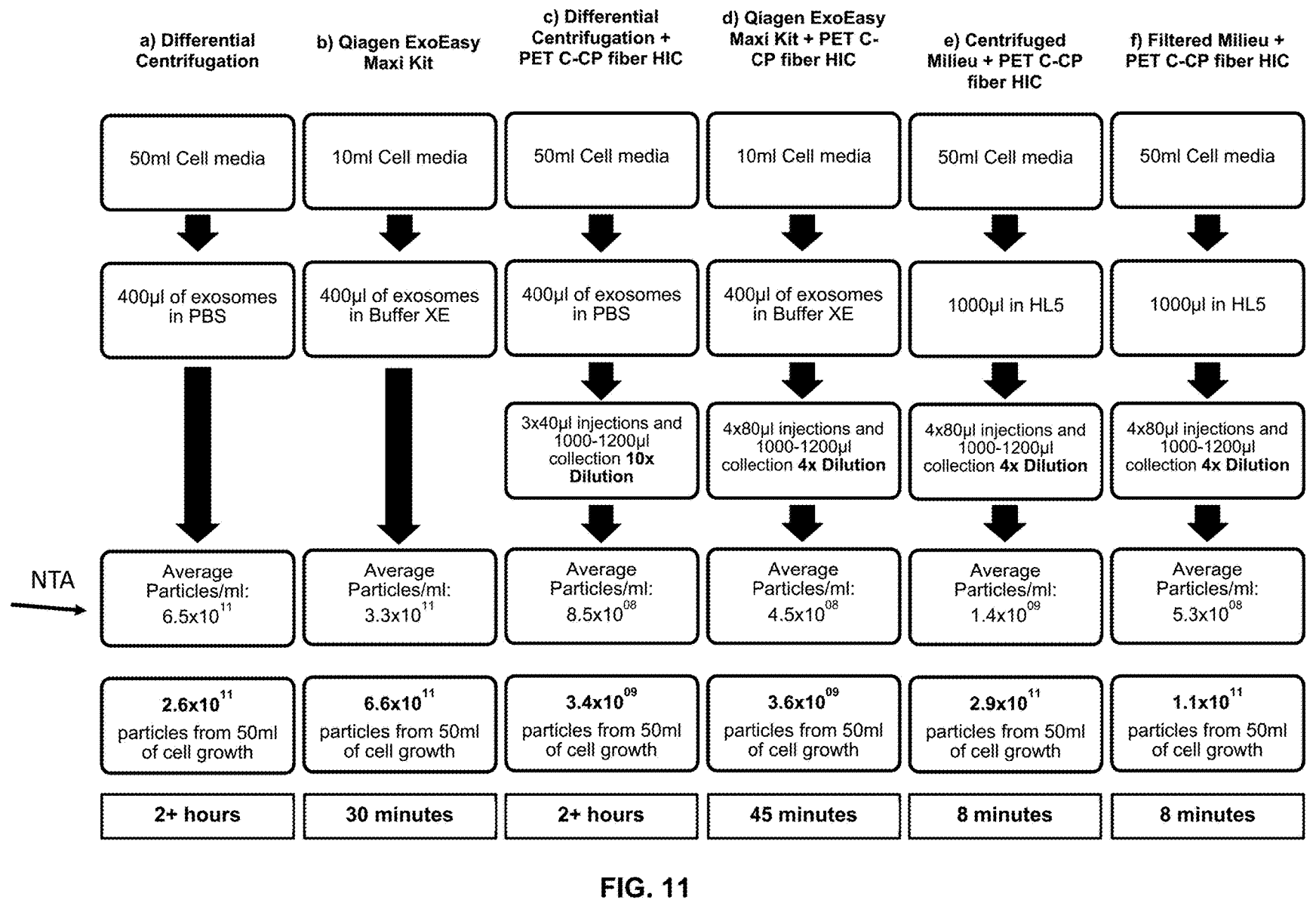

| | a) Differential Centrifugation | b) Qiagen ExoEasy Maxi Kit | c) Differential Centrifugation + PET C-CP fiber HIC | d) Qiagen ExoEasy Maxi Kit + PET C-CP fiber HIC | e) Centrifuged Milieu + PET C-CP fiber HIC | f) Filtered Milieu + PET C-CP fiber HIC |
|---|---|---|---|---|---|---|
| | 50ml Cell media | 10ml Cell media | 50ml Cell media | 10ml Cell media | 50ml Cell media | 50ml Cell media |
| | 400µl of exosomes in PBS | 400µl of exosomes in Buffer XE | 400µl of exosomes in PBS | 400µl of exosomes in Buffer XE | 1000µl in HL5 | 1000µl in HL5 |
| | | | 3x40µl injections and 1000-1200µl collection **10x Dilution** | 4x80µl injections and 1000-1200µl collection **4x Dilution** | 4x80µl injections and 1000-1200µl collection **4x Dilution** | 4x80µl injections and 1000-1200µl collection **4x Dilution** |
| NTA | Average Particles/ml: $6.5x10^{11}$ | Average Particles/ml: $3.3x10^{11}$ | Average Particles/ml: $8.5x10^{08}$ | Average Particles/ml: $4.5x10^{08}$ | Average Particles/ml: $1.4x10^{09}$ | Average Particles/ml: $5.3x10^{08}$ |
| | **$2.6x10^{11}$** particles from 50ml of cell growth | **$6.6x10^{11}$** particles from 50ml of cell growth | **$3.4x10^{09}$** particles from 50ml of cell growth | **$3.6x10^{09}$** particles from 50ml of cell growth | **$2.9x10^{11}$** particles from 50ml of cell growth | **$1.1x10^{11}$** particles from 50ml of cell growth |
| | **2+ hours** | **30 minutes** | **2+ hours** | **45 minutes** | **8 minutes** | **8 minutes** |

FIG. 11

CHANNELED FIBERS IN SEPARATION OF BIOLOGICALLY ACTIVE NANOPARTICLES

CROSS REFERENCE TO RELATED APPLICATION

This application is a Continuation Application, which claims priority to U.S. patent application Ser. No. 16/267,579, having a filing date of Feb. 5, 2019, which claims filing benefit of U.S. Provisional Patent Application Ser. No. 62/626,398 having a filing date of Feb. 5, 2018, both of which are incorporated herein by reference for all purposes.

STATEMENT WITH REGARD TO FEDERALLY SPONSORED RESEARCH AND DEVELOPMENT

This invention was made with government support under CHE-1608663 awarded by the National Science Foundation. The government has certain rights in the invention.

BACKGROUND

Biologically active structures on the nanometer scale, i.e., nanoparticles, both natural and synthetic, have been proposed for a myriad of uses including disease diagnosis, drug delivery, tissue regeneration, gene therapy, and cancer therapies, among others. Natural biologically active particles include, for example, bacteria, virus particles, whole cells, prions, and cellular components such as individual organelles, DNA, RNA, vacuoles, exosomes and lysosomes. Synthetic biologically active nanoparticles include, for example, delivery materials such as liposomes and genetically modified virus particles and bacteria for use in plasmid delivery.

There are many types of bio-nanoparticles that may be isolated and manipulated for various purposes. For instance, isolation of exosomes is just one of many examples of bio-nanoparticles of interest for characterization as well as possible utilization. Exosomes are lipid membrane-derived vesicles, approximately 30-100 nm in size, that are secreted by most cell types. As exosomes are released by many cell types, they can be found in most body fluids, including urine, saliva, amniotic fluid, semen, breast milk, plasma, mucus, and blood. They hold a great deal of promise in disease diagnostics and drug delivery, among other uses, as they have been shown to display the same protein biomarkers as their originating cell. These biomarkers can serve as protein "fingerprints" that can harold the presence of diseased cells within the body (e.g., cancer cells, etc.), potentially long before disease symptoms arise. As the basic understanding of exosomes is still in its early stages, many of these potential applications are yet to be realized.

In order for many nanoparticle-based uses to become a reality, efficient and reliable methods for isolating and concentrating the nanoparticles are required. Unfortunately, most of the current isolation techniques require long processing times or expensive equipment. For example differential centrifugation (DC), a widely used particle isolation technique, is generally considered the gold standard for isolation of exosomes as well as other biological nanoparticles. DC requires the use of a high speed centrifuge, which can be cost prohibitive to many clinics. In addition, the process takes several hours to complete and has been shown to not only sediment the desired particles, but can also alter the integrity of the lipid bilayer membrane of natural particles (e.g., exosomes, encapsulated virus, whole cells, etc.) during resuspension, making many uses (e.g., miRNA readings) unreliable. Furthermore, the high speed centrifugation process often causes the particles to form self-aggregates and to aggregate and co-sediment with large amounts of protein and other cellular components.

Other nanoparticle isolation techniques include density gradient centrifugation, size exclusion chromatography, ultrafiltration, polymer-based precipitation, immunological separation, and microfluidics isolation techniques. Some of these methods are generic with respect to the specific types of nanoparticles which can be isolated, while others solely capture vesicles originating from specific cell types. Unfortunately, none of the current nanoparticle isolation techniques are sufficient for use in clinical diagnostics or for isolation of larger lots from cell culture media as would be required for, e.g., drug delivery applications.

Capillary-channeled polymer fibers have been extensively studied for separations such as bio-macromolecule (e.g., proteins) separations. Such fibers are generally manufactured by melt-extruding a polymeric composition with the desired channeled morphology including multiple capillary channels extending the entire length of the fiber. The morphology of the channeled fibers gives the fibers a much greater surface area as compared to circular cross-sectional fibers with the same diameters. When packed in columns, capillary-channeled fibers can self-align and can yield a monolith-like structure with open, parallel channels. These channels provide excellent fluid transportation properties and low mass transfer resistance in the columns. It is believed that the high column permeability, low mass transfer resistance and the low cost of the channeled fiber chromatography columns make them promising choices for fast separations at various scales.

What are needed in the art are methods and materials for use in isolating and concentrating biologically active nanoparticles.

SUMMARY

According to one embodiment, disclosed is a method for separating biologically active nanoparticles from a mixture. More specifically, disclosed is a hydrophobic interaction chromatography (HIC) method that can be used to separate biologically active nanoparticles from other materials (including other nanoparticles) present in a mixture.

A method can include flowing a mobile phase through a fluid conduit having a first end and a second end that is disposed opposite the first end. The mobile phase includes a salt, for instance in a concentration of from about 1 M to about 3 M. The fluid conduit contains a solid phase that defines passages that allow flow of nano-sized particles through the conduit, generally from about 1 micrometer to about 4 micrometers. In one embodiment, the solid phase includes a fiber comprising a plurality of co-linear channels on the outer surface of the fiber and extending along the axial length of the fiber that provides flow passages of the desired size through the conduit. In general, the solid phase has little to no porosity in its own right such that the solid phase is essentially non-porous to the nanoparticles to be captured by the system. For instance, the solid phase can have a porosity of about 500 Angstroms or less. As such, the passages through the conduit are external to the material forming the solid phase, e.g., through channels formed along the surface of the solid phase and/or between individual solid phase segments. In one embodiment, the solid phase has a moderately hydrophobic surface. For instance, the solid phase can exhibit a critical surface tension of about 35 mJ/m$^2$ or greater and a water contact angle of about 85° or less.

A method can also include adding a mixture to the mobile phase, for instance by injecting the mixture into the mobile phase prior to or as the mobile phase flows from the first end to the second end of the fluid conduit. The mixture includes biologically active nanoparticles and as the mobile phase flows through the fluid conduit, the biologically active nanoparticles can adsorb to the hydrophobic surface of the solid phase due to the kosmotropic effect of the salt in the mobile phase.

Following, the salt concentration of the mobile phase can be decreased, for instance by a gradual reduction over a period of time. As the salt concentration is reduced, the biologically active nanoparticles can be released from the surface of the fibers, and the nanoparticles can be collected following exit of the flow from the second end of the fluid conduit.

Beneficially, the methods can be used to quickly and efficiently separate biologically active nanoparticles from other components in a mixture, including materials that can be very difficult to separate from one another according to previously known separation methodologies such as other biologically active nanoparticles and proteins.

Additional objects and advantages of the invention will be set forth in the description which follows. The objects and advantages of the invention may be realized and attained by means of the instrumentalities and combinations particularly pointed out in the appended claims.

BRIEF DESCRIPTION OF THE DRAWINGS

The disclosed subject matter may be better understood with reference to the drawings in which:

FIG. 11 provides a comparison of nanoparticle tracking analysis (NTA)-determined particle population characteristics following various exosome isolation methodologies.

DETAILED DESCRIPTION

Figure 1:
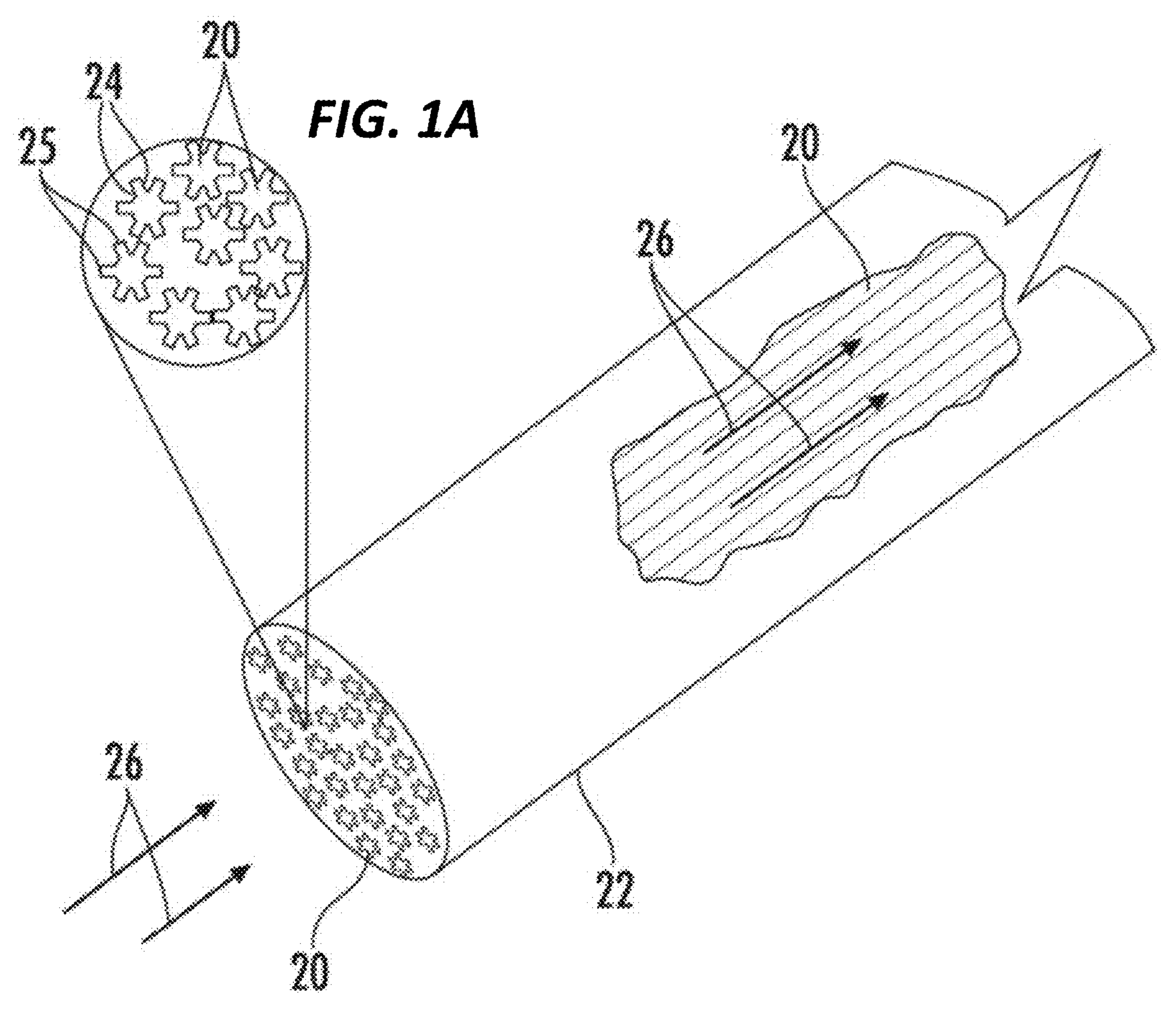
FIG. 1 is a representation of a liquid flowing through a conduit containing a plurality of channeled polymeric fibers and including at FIG. 1A a cross-sectional view inset showing the end-on shape of representative channeled polymeric fibers and at FIG. 1B a cross-sectional view inset showing the end-on representation of hollow polymeric fibers.

Reference now will be made in detail to embodiments of the disclosed subject matter, one or more examples of which are illustrated in the accompanying drawings. Each example is provided by way of explanation of the subject matter, not limitation of the subject matter. In fact, it will be apparent to those skilled in the art that various modifications and variations can be made in the disclosed embodiments without departing from the scope or spirit of the subject matter. For instance, features illustrated or described as part of one embodiment, can be used on another embodiment to yield a still further embodiment. Thus, it is intended that the present disclosure cover such modifications and variations as come within the scope of the appended claims and their equivalents.

The present disclosure is generally directed to a relatively fast, inexpensive, and non-destructive method for separation and isolation of biologically active nanoparticles. More specifically, the methods include the use of a hydrophobic interaction chromatography (HIC) protocol to isolate biologically active nanoparticles from other components of a mixture, including, e.g., other biologically active nanoparticles, proteins, cellular debris, etc. The methods can be used to isolate nanoparticles with comparable yields and size distributions when compared to other, more traditional methods of nanoparticle isolation, but can do so on a much shorter time scale. Furthermore, the versatility of materials that can be used to form the solid phase of a system can provide a facile approach for surface modifications that can be used to further enhance the isolation protocols, for instance to provide for exosome type-specific isolation, e.g., for use in medical diagnostic applications. In some embodiments, methods can include post-capture processing of the captured nanoparticles. For instance, following isolation, captured nanoparticles can be subjected to further processing such as lysing to release the contents of the nanoparticles. Captured nanoparticles and/or the released content thereof can be subjected to molecular testing and characterization including, without limitation, protein, DNA, and RNA sequencing and analysis. Captured nanoparticles can also be subjected to selective labeling and optical probing to confirm the nanoparticles' identity. The solid phase chosen for the separation protocols can also be selected so as to provide for scalable separations, allowing for small, spin-down columns as well as preparative scale operations for bulk isolations of products prepared in bioreactors, for instance, for use in preparation of drug delivery vehicles.

The disclosed HIC approach for separation nanoparticles, can provide improvements over previously known separation methods such as reversed-phase methods as commonly used in molecular separations. For instance, the level of organic solvents employed in reverse-phase separation methods can have adverse effects on the structural integrity of biologically active nanoparticles, particularly those having a lipid bilayer exterior such as exosomes, lysosomes, and liposomes. Moreover, separation protocols that incorporate high levels of organic solvents such as reverse-phase methods can lead to the loss of species (e.g. proteins) adhered to the surface of the nanoparticles, thereby limiting the purity of the isolated nanoparticles and the chemical and structural integrity of those species.

The disclosed methods also provide improvements by use of a stationary phase that provides a well-controlled throughput. For instance, in one embodiment, the stationary phase can be formed of shaped fibers that are formed with a cross sectional shape that defines flow channels along the outer surface of the length of the fibers. In addition, the bulk fibers themselves can be essentially non-porous (e.g., porosity of the bulk fiber of about 500 Angstroms or less). As such, any porosity of the bulk fiber can be too small for flow interference, and specifically too small for capture or internal passage of the nanoparticles of interest into the bulk fiber. In terms of hydrodynamics, the external channeled structure of such fibers allows for excellent flow characteristics of culture media (e.g., low backing pressure at high flow rates), while also providing a high surface area for contact between the mobile and stationary phases. Moreover, as the fibers can be essentially non-porous, the solid phase material can avoid particle entrapment, clogging, and loss of product within the bulk fiber material itself. As such, a sample may be processed in a shorter amount of time as compared to previous separation methods with high recovery and little or no chance of conduit clogging.

Disclosed processes can be utilized in separation and isolation of natural as well as synthetic biologically active nanoparticles that include a hydrophobic surface, including, without limitation, bacteria, virus particles, prions, whole cells, exosomes, lysosomes, lipoproteins, liposomes, and genetically modified particles. In one embodiment, the methods can be utilized for separation of vesicles that include a lipid bilayer enclosure, e.g., exosomes, lysosomes, liposomes, vacuoles, prions and virus including an encapsulating lipid envelope, etc. The methods can be highly effective in separation and isolation of membrane-enveloped nanoparticles by virtue of the nature of the lipid-based exterior of such nanoparticles. However, the methods are not limited to biologically active nanoparticles having a lipid bilayer exterior, and the methods can be utilized in separating biologically active nanoparticles having a different type of exterior surface, e.g., bacterium including an exterior cell capsule, non-enveloped virus particles, prions, lipoproteins and lipoprotein-like nanoparticles, etc.

The methods, can beneficially be utilized to separate biologically active nanoparticles from other materials that may be present in any sample. As used herein, the term "sample" generally refers to any mixture suspected of containing the biologically active nanoparticles of interest. A sample may be derived from any biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used such as water, cell culture media, food products, and so forth, for the performance of in vitro assays. A sample may be used directly as obtained from the source or following a pretreatment to modify the character of the sample. For example, such pretreatment may include preparing plasma from blood, diluting viscous fluids, and so forth. Methods of pretreatment may also involve filtration, centrifugation, precipitation, dilution, distillation, mixing, concentration, inactivation of interfering components, the addition of reagents, lysing, etc.

The solid phase of the HIC separation protocol can define passages through an HIC system that are of a size to allow flow of a media carrying the targeted nanoparticles as indicated in FIG. 1 at 26. In general, passages through a system can have a cross sectional size of from about 1 μm or greater, for instance from about 1 μm to about 4 μm in some embodiments. While the passages through a system can vary in cross sectional dimension along the length of the system, they can generally have a dimension of about 1 μm or greater so as to allow flow of a nanoparticle-containing media without clogging. In addition, the solid phase can encourage suitable contact between the targeted nanoparticles and the solid phase. As such, larger passages through the system can generally be avoided.

Figure 1B:
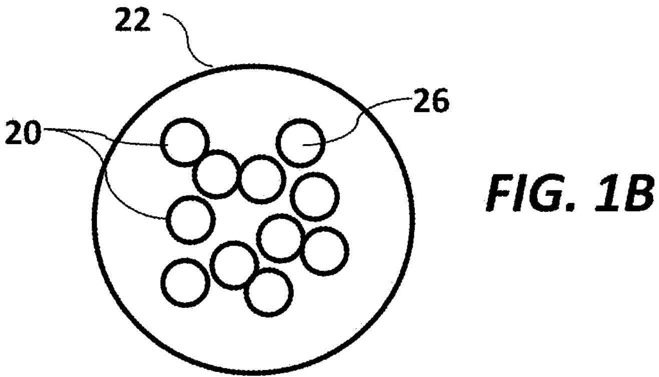

In one embodiment, the solid phase can include fibers or particles that are packed together so as to define passages between adjacent components. Hollow fibers define a hollow core having the desired passage dimensions are also encompassed. In such an embodiment, media can be caused to flow only through the hollow core or alternatively, both within the hollow core and along the external surface of the fibers, with passages 26 being defined by the packing of the adjacent fibers 20 (FIG. 1B). In any case, however, when utilizing hollow fibers, the fiber material itself can be nonporous to the nanoparticles targeted by a system, as discussed previously, such that nanoparticles will be captured on the surfaces of the fibers, and not within pores formed within the fiber walls.

In one embodiment illustrated in FIG. 1, the solid phase can include fibers having a non-circular cross-sectional geometry. The non-circular cross-sectional geometry arises from channels extending axially and continuously on the exterior of the fiber surface and generally along the entire length of each fiber. In one embodiment, each fiber can have a uniform diameter (measured at the largest cross-sectional point-to-point location) along the axial length of the fiber in the range of about 20 to about 50 micrometers.

As illustrated in FIG. 1, in one embodiment bundles of fibers 20 can be packed into a conduit 22 (e.g., a stainless steel tube having a uniform circular inside diameter of about 0.25 inches and a length of about 12 inches). The dimensions of the conduit 22 can be any size and its composition either metal or polymeric. In general, the length of each fiber 20 can be substantially the same as the length of the conduit 22 and can be disposed to extend within the conduit 22 over substantially the entire length of the conduit 22. However, fibers 20 that have lengths that are shorter or longer than the length of the conduit 22 may be used.

As shown schematically in cross-section in the expanded view inset of FIG. 1A, each fiber strand 20 can have six co-linear channels 24 extending the entire length of the exterior surface of the fiber 20. Each channel 24 is defined by a pair of opposed walls 25 that extend generally and longitudinally and form part of the exterior surface of the fiber 20. The channels 24 and walls 25 can extend down the entire length of the fiber 20 parallel to the longitudinal axis of the fiber 20 and are co-linear on each fiber 20. This produces de facto substantially the same co-linear channels 24 along the entire length of the conduit 22.

It should be understood that the particular shapes of the channeled fibers illustrated in FIG. 1 are not a requirement of the present disclosure. In particular, the number and/or cross-sectional shape of the channels as well as the overall shape of the channeled fibers can vary from that shown in the figures.

Figure 2:
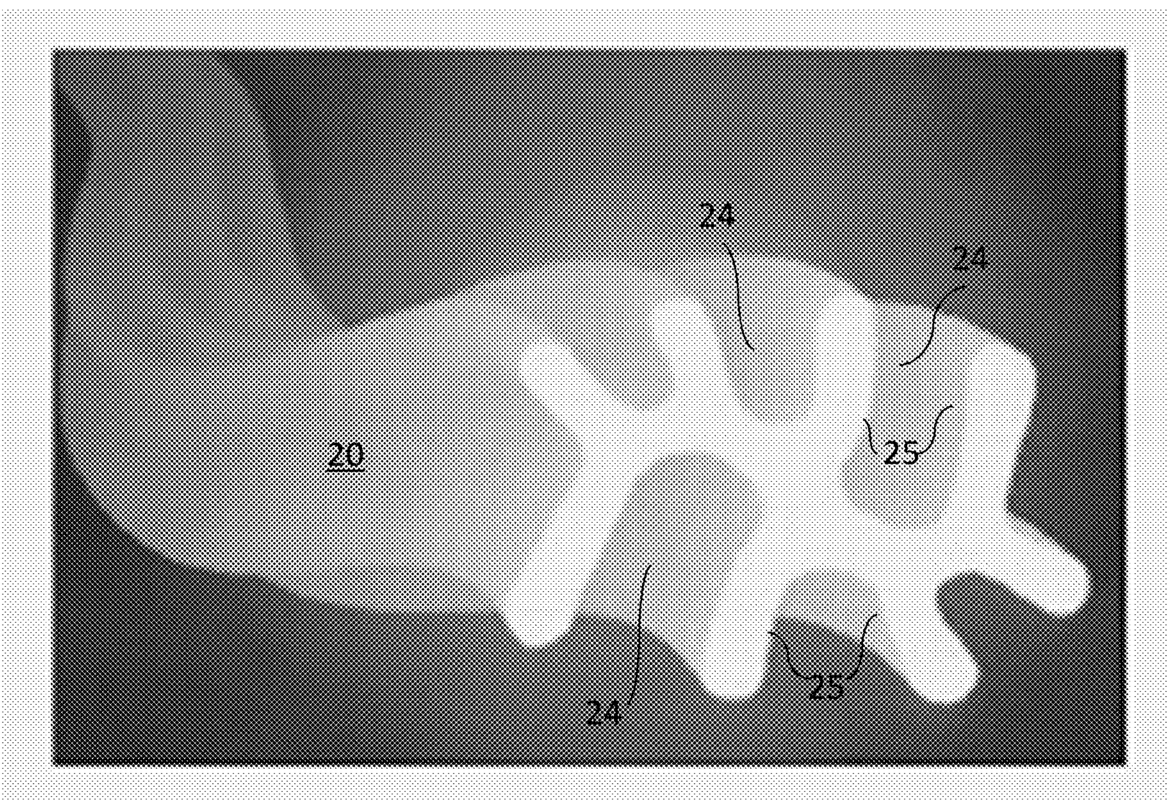
FIG. 2 is a schematic representation of one embodiment of a channeled polymeric fiber as may be utilized in disclosed methods.
Figure 3:
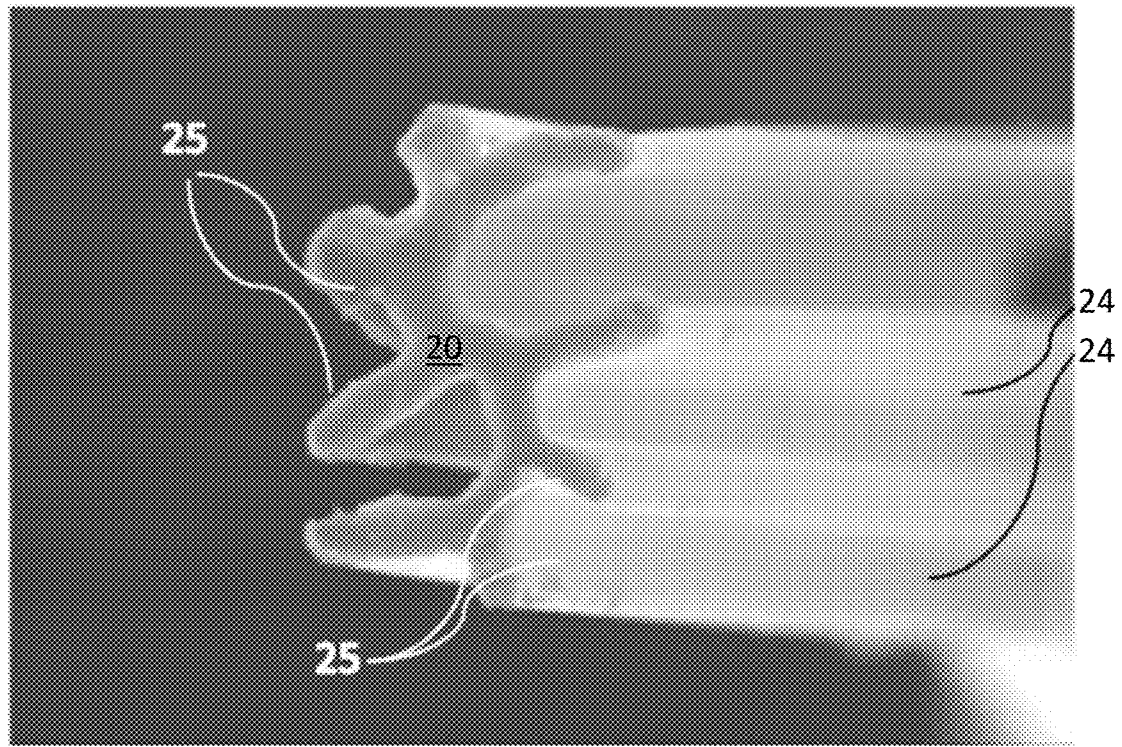
FIG. 3 is a perspective view of an end of a single channeled polymeric fiber.

For instance, FIG. 2 illustrates a channeled fiber 20 that includes eight co-linear channels 24 extending the entire length of the exterior surface of the fiber 20. As with the embodiment of FIG. 1A, each channel 24 is defined by walls 25 that extend generally and longitudinally and form part of the exterior surface of the fiber 20. FIG. 3 illustrates a single fiber 20 in perspective view showing the eight individual capillary channels 24 that are open at the fiber surface and defined by opposing walls 25 that form a portion of the fiber exterior surface.

In one embodiment, the channels 24 can be configured to wrap around the length of the fiber 20 in a helical fashion. As such, the channels 24 of the fibers 20 can follow a helix pattern. In those embodiments in which a plurality of fibers are combined in a single separation column, the fibers can be axially twisted such that the channels wrap around the axis of each fiber and the helix pattern of the multiple fibers can all have substantially the same helical pitch. (The pitch is the number of complete turns of a channel 24 around the axis of a fiber 20 per unit of length of the fiber 20.) In this case, a fiber will still include de facto a plurality of substantially identical co-linear channels 24 along the entire length of each fiber 20 and thus also along the entire length of a conduit 22.

Figure 4:
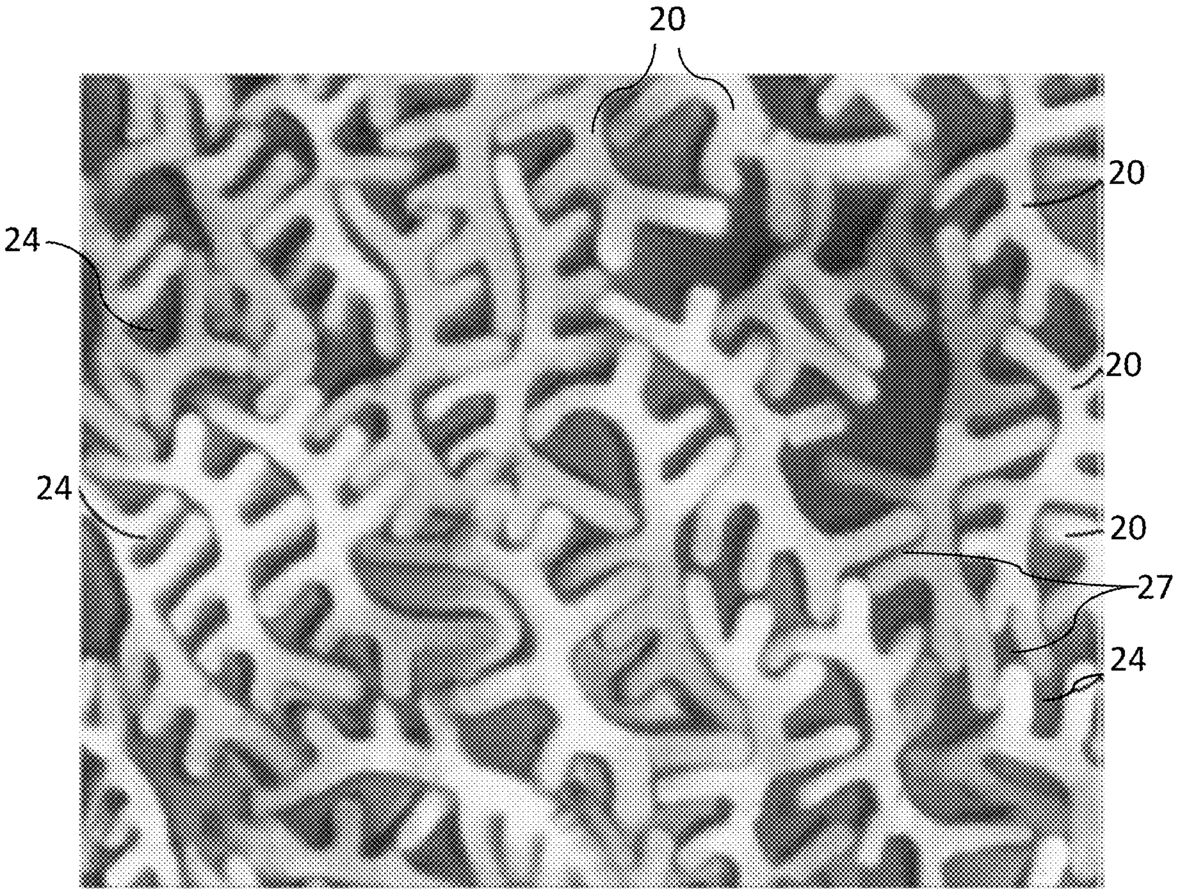
FIG. 4 presents a cross-sectional view of a plurality of channeled polymeric fibers packed together.

In the course of packing a plurality of fibers 20 into a bundle, e.g., a bundle that lays along the entire length of a conduit 22, channels can also be formed between adjacent fibers. For instance, FIG. 4 presents a cross-sectional view of a plurality of channeled fibers packed together, as in a casing for a separation device. As shown, each fiber 20 has a plurality of co-linear channels 24 extending along the axial length of the exterior surface of the fiber 20. In addition, channels (or capillaries) 27 can be formed between adjacent fibers, which can add to the overall fluid movement characteristics of a bundle of fibers 20. As such, when packed in column formats, the inter-digitated fibers can create massive numbers of parallel channels (e.g., from about 1 to about 4 micrometers in width) that can provide high permeability to fluid flow.

Advantageous in the use of channeled fibers 20 as solid phase materials is their very high surface area-to-volume ratios versus circular cross section fibers. The shape and the number of channels 24 can be dependent on achieving the desired attribute of very high surface area-to-volume ratios. In this regard, the inclusion of helical channels in which the fibers can define an axial twist along the length of the conduit can pack more surface area into that column than the linear channels.

Another advantage of using channeled fibers 20 for separations is the fact that they generate very low backing pressures (e.g., about 500 to about 1000 psi for linear channels) for normal chromatography flow rates (e.g., about 0.5 mL/min to about 3 mL/min). The lower backing pressure produced in a conduit 22 containing channeled fibers 20 relative to the backing pressure produced in the conventional column containing beads, is believed to be due to the parallel-running channels 24.

Figure 5:
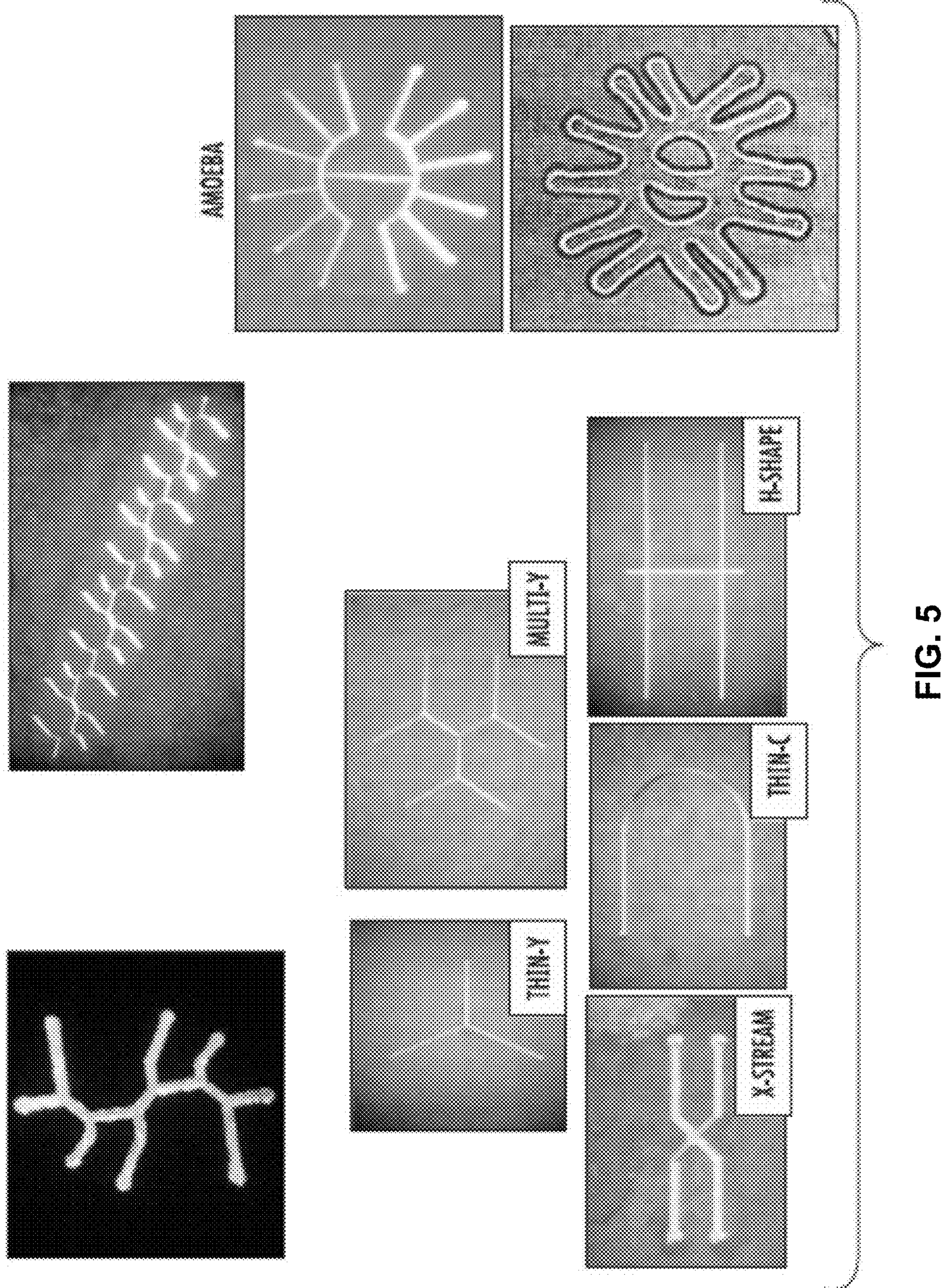
FIG. 5 illustrates several different examples of channeled polymeric fibers and spinnerets therefore.

It should be understood that the particular shapes of the channeled fibers illustrated in FIGS. 1-4 are not a requirement of the present disclosure. In particular, the number and/or cross-sectional shape of the channels as well as the overall shape of the channeled fibers can vary from that shown in the figures. For instance, the depth of a single channel on a fiber, i.e., the radial height of walls 25 can vary, for instance, from about 1 μm to about 20 μm in some embodiments. By way of example and without limitation, FIG. 5 presents several different variants of channeled fibers as are encompassed herein.

In addition, it should be understood that disclosed methods are not limited to utilization of bundles of channeled fibers. In one embodiment, a single channeled fiber can be used in single fiber separations. For example the solid phase of a separation protocol can take the form of a single fiber in-laid in a micro-machined device. By extension, a flat-format fiber/film such as that illustrated in FIG. 5, having a plurality of channels linearly adjacent to one another is encompassed. Such channels could affect many of desirable transport and chemical attributes of an HIC system.

The stationary phase can include a surface having a hydrophobicity that can adsorb biologically active nanoparticles contained in the mobile phase and release the biologically active nanoparticles upon variation in the conditions of the system. For instance, upon variation in the salt concentration of the mobile phase. In one embodiment, the stationary phase can be formed of a polymeric composition that includes a moderately hydrophobic polymer or that can be surface modified to provide the desired hydrophobic characteristics to the surface. For instance, a channeled fiber stationary phase can have a surface that exhibits a critical surface tension of about 35 $mJ/m^2$ or greater and a water contact angle of about 85° or less, for instance a critical surface tension of about 37 $mJ/m^2$ and a water contact angle of about 80° or less in some embodiments. For instance, critical surface tension can be determined by the Zisman method (regression of the cosine of the contact angle), or by the wetting tension method (using solutions of 2-ethoxyethanol and formamide, per ASTM Std. D-2578), and water contact angle can be determined by ASTM Std. D-7334.

Variation in the polymeric composition used in forming the stationary phase can permit the "chemical tuning" of the separation process, for instance through modification of the hydrophobic qualities of the surface, through modification of the mobile phase during a process, or through other surface modification as discussed further herein.

A stationary phase can be formed from a polymeric composition including one or more polymers having moderate hydrophobic characteristics. Representative polymers can include, without limitation, polyvinyl alcohol, nylon (e.g., nylon 6; nylon 6,6; nylon 7,7; nylon 8,8; nylon 9,9, nylon 12; nylon 11), polyethylene glycol, polysulfone, polymethyl methacrylate, polyethylene terephthalate, polyepoxies, polyoxymethylene, polyvinylidone chloride, polyphenylene sulfide, acrylonitrile butadiene styrene, polycarbonate, polyvinyl chloride, and polyvinyl acetate.

The combination of macro (e.g., bulk flow characteristics) and micro (essentially non-porous) characteristics possible for the stationary phase can result in the ability to affect separations of biologically active nanoparticles at exceedingly high linear velocities (>50 mm $sec^{-1}$) without the mass transfer limitations common to traditional porous phases. Moreover, the hydrodynamic advantages can be complemented by a very high degree of chemical separation diversity.

Various fabrication approaches can be used to form channeled fibers of a stationary phase. A formation process can generally include any that is amenable to polymeric compositions as may be used in formation of the fibers. For example, channeled fibers 20 may be melt spun from a polymeric composition that includes any of a number of different polymers or polymer precursors. In one embodiment, the polymeric composition can include formed polymers, and in other embodiments the polymeric composition can include polymeric precursors that can be polymerized during/following formation of the fibers.

In addition to the range modalities of separation that can be affected using different base polymers, an extensive tool box of simple surface modification approaches can also be utilized in design of a separation system. For instance, the surface of the solid phase may be modified to including binding agents specific for the targeted nanoparticles. A solid phase surface may be modified to include high ligand densities for ion exchange (cationic and anionic) and affinity chromatography so as to improve capture of the desired nanoparticles. Affinity separations can be carried out through the addition at the surface of the solid phase immobilized ligands such as, without limitation, antibodies or aptamers, biotin-streptavidin interactions, and chelates for immobilized metal affinity chromatography (IMAC) or other specific binding agents as discussed elsewhere herein. Such attributes make the utilization of channeled polymer fibers for biologically active nanoparticle isolation a useful alternative to traditional isolation methodologies.

Surface modifications can be carried out on the solid support phase according to any suitable methodology. For example, in one embodiment, a predetermined chemical reactivity can be obtained by modifying at least portions of the surfaces of the polymeric surface of a formed fiber to a predetermined level of hydrophobicity. Thus, active sites on the fiber surfaces can be functionalized to gain more or less hydrophobic character.

In another embodiment, a predetermined chemical reactivity also can be obtained by modifying at least portions of the surface of the support phase to a predetermined ionic character. For example, surfaces of fibers can be protonated in situ by an acidic mobile phase.

Surface modification can be carried out on all or a portion of a stationary phase. For instance a first area of a fiber can be modified to exhibit a predetermined hydrophobic character and a second area of the fiber can be modified to include a predetermined ionic character. Alternatively, a single or multiple modifications can be carried out over the same surface of a fiber.

As mentioned, in one embodiment a bundle of channeled fibers can be combined in a fluid conduit in formation of a separation system. In one embodiment, manual packing can be utilized to locate the bundle of fibers into the conduit, e.g., a steel tube conduit 22 as depicted schematically in FIG. 1. However, any reliably reproducible way of packing a conduit with the support/separation phases can be utilized in order to mass-produce columns.

In one embodiment, radial compression technologies can be employed to affect uniform packing of the fibers 20. For example, the tubing can be formed of a polymeric composition including e.g., polyethylene terephthalate (PET), and the resulting conduit 22 then can be surrounded by a water jacket. Increases in pressure applied to the jacket can squeeze the conduit 22 and thus compress the fibers 20 into a tighter bundle.

The mobile phase used in a separation can include components to affect the initial adsorption of the targeted species. For instance, a mobile phase can initially include a salt concentration to encourage the desired interaction between a moderately hydrophobic solid phase and the targeted species and affect adsorption of biologically active nanoparticles of the mobile phase onto the surface of the solid phase. Through combination of the hydrophobic characteristics of the solid phase (that can optionally include surface modification) and the variation in a salt content/concentration of the mobile phase during a separation protocol, disclosed systems can provide very efficient solution mass transfer for highly selective separations of biologically active nanoparticles.

In one embodiment, the mobile phase used to introduce a targeted species into the separation system can include a dissolved alkali salt. While any suitable salt system as is known in HIC can generally be utilized, in one embodiment the initial mobile phase can include a sulfate salt such as ammonium sulfate or sodium sulfate. In this embodiment, the anions present in the mobile phase during the adsorption of the biologically active nanoparticles to the surface of the solid phase will be sulfate ions, which are strongly lyotropic. In one embodiment, the concentration of the salt (or combination of salts) can be about 3.0 M or less, for instance from about 1 M to about 3 M, or about 2.5 M in some embodiments. As one of skill in the art will realize, the upper salt concentration can be determined by the solubility of the particular salt(s) of the initial mobile phase. However, different salt concentrations and/or the addition of organic modifiers can be utilized in different applications, not only depending on the specific characteristics of the channeled fibers, but also on the characteristics of the nanoparticles to be separated.

Organic modifiers can be included in a mobile phase in one embodiment. Organic modifiers can prevent or reduce chemical and/or physical instability of the nanoparticles during a protocol. Addition of an organic modifier in a mobile phase can allow for a decrease in salt concentration of the mobile phase without loss of function of the system. Beneficially, integrity of capture nanoparticles (e.g., lipid bilayer-containing nanoparticles such as exosomes) can also improve with addition of an organic modifier to the mobile phase. Organic modifiers can include, but are not limited to, organic solvents such as acetonitrile, alcohols (e.g., methanol), polyols (e.g., glycerol), and combinations thereof.

When included, an organic modifier can generally be incorporated in a mobile phase in an amount of about 50 wt. % or less, with the preferred amount depending upon the specific characteristics of the system. For instance, a polyol, such as glycerol can be incorporated in a mobile phase at an amount of about 50 wt. % or less, while an organic solvent such as acetonitrile may generally be incorporated in a mobile phase at a lower concentration, for instance in an amount of about 30 wt. % or less.

The pH of the mobile phase during the adsorption step may differ from the pH during the elution of the separation nanoparticles. However, in general, and to ensure the stability of the targeted biologically active nanoparticles, the pH can remain at physiological pH, e.g. in the range of about 6.5-8.5 throughout a protocol.

To affect a separation protocol, a sample including the targeted biologically active nanoparticles can be combined with the initial mobile phase. The combination can be carried out prior to feeding the mobile phase to the separation conduit or as the mobile phase is fed to the conduit (e.g., via injection to the flowing mobile phase).

In some embodiments, a device can be provided to move fluid through the conduit, and thus through the channels 24 of the fibers 20. A pump (not shown in the figures) is typically provided for this purpose. The flow of liquid through the conduit 22 is schematically indicated by the arrows designated by the numeral 26 in FIG. 1. In general, and for the purpose of providing high flow rates of liquid 26 through the conduit 22 along the fibers 20 can be arranged with their longitudinal axes parallel to the longitudinal axis of the conduit 22.

In some applications, movement of a fluid may be effected without a device that is separate from the support phase. In such embodiments, the fluid can move through the passages of the conduit, e.g., through the channels 24 of the fibers 20 solely by capillary action of the channels 24 of the fibers 20. In yet another embodiment, a fluid can be fed through a device by use of centrifugal force. For instance, a device (e.g., a small micropipette tip-type device that incorporates only one or a few fibers) can be held in conjunction with the fluid and rapidly spun by use of a centrifuge so as to force the fluid through the device. The fluid, which can carry the biologically active nanoparticles and/or other materials of use in a process (e.g., a detectable label or the like) can interact with the fibers during/following the spinning.

As the fluid passes through the column and interacts with the solid phase, the biologically active nanoparticles can adsorb to the surface of the solid phase via hydrophobic interaction. In some embodiments, following a period of contact during which the biologically active nanoparticles can adsorb to the surface of the channeled fibers (e.g., generally about 3 minutes or less, for instance from about 0.5 minutes to about 10, though a particular adsorption period can vary depending upon, e.g., the sample size, the mobile phase flow rate, the system size, etc.).

In some embodiments, an on-fiber imaging approach (e.g., fluorescent imaging, visual imaging, etc.), optionally combined with one or more other techniques, can be carried out prior to or absent elution of the nanoparticles from the fibers. For instance, following adsorption of the biologically active particles to the fibers, a second fluid carrying a detectable label (e.g., a fluorescent marker) can be passed through the column (e.g., via pumping, centrifugation, wicking, etc.) and the detectable label can be attached to the adsorbed nanoparticles. Such an approach can provide for on-fiber imaging prior to any elution to remove the nanoparticles from the fiber(s).

In one embodiment, following adsorption of the nanoparticles to the solid phase, the adsorbed materials can be examined while on the solid phase, for instance either prior to or even absent elution. For instance, following adsorption, a mobile phase can carry a detectable label that can specifically bind to adsorbed materials. Detectable labels can be designed to specifically bind to only a single type of adsorbed nanoparticle (e.g., only exosomes carrying a particular binding agent) or to a plurality of different types of nanoparticles (e.g., all nanoparticles that incorporate a lipid bilayer). Optionally, a mobile phase can deliver a plurality of detectable labels, each designed to specifically bind to only certain of the adsorbed nanoparticles.

A detectable label may be any one of a wide variety of detectable labels. In one particular embodiment, a detectable label can provide a color change to the targeted nanoparticle, which can be either a visible color change, or one that requires an instrument to detect the change in color. As representative examples of detectable labels, which may or may not require an instrument for detection, there may be mentioned various chromogens, such as fluorescent materials, phosphorescent materials, dyes, and the like.

In some instances, it is desired to modify the detectable label in some manner so that they are more readily able to bond to the adsorbed nanoparticles of choice. In such instances, the detectable label may be modified with certain specific binding members to form conjugated detection probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies, and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. Other common specific binding pairs include but are not limited to, biotin and avidin, biotin and streptavidin, antibody-binding proteins (such as protein A or G) and antibodies, carbohydrates and lectins, complementary nucleotide sequences (including label and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the detectable label using any of a variety of well-known techniques. For instance, covalent attachment of the specific binding members to the labels may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished.

In one embodiment, following adsorption and any on-fiber examination, rather than elution of the complete nanoparticles, the nanoparticles can be lysed, with collection of the nanoparticle contents. According to this embodiment, a mobile phase can be carried through the system that can carry a lysis solution. The term "lysis solution" refers to a solution containing a substance that lyses the nanoparticles, e.g., exosomes, such as a surfactant, a buffer solution of potassium ethyl xanthogenate, or lysozyme, but the substance is not limited thereto. Examples of surfactants include SDS (sodium dodecylsulfate), Triton X-100, or cetyl trimethyl ammonium bromide (CTAB), but are not limited thereto.

In one embodiment, following adsorption, the adsorbed nanoparticles can be eluted off of the solid phase. In this embodiment, the mobile phase can be modified to decrease the salt content of the mobile phase. As discussed above, the disclosed channeled fiber-based HIC method can be considerably faster than previously known HIC separation protocols, a major asset with regards to potential usefulness for nanoparticle isolation in a clinical setting. For example, when utilizing a single step-gradient process, the HIC method can be carried out in just a few minutes, e.g., less than about 3 minutes.

While the change in mobile phase for elution can be carried out in one or more relatively instantaneous steps, e.g., from a first adsorption mobile phase to a second elution mobile phase in a defined single step, in one embodiment, the decrease in salt content of the mobile phase can be carried out gradually, with a decrease (either linear or non-linear) in the salt concentration of the mobile phase over a period of time.

At a lower salt concentration, the biologically active nanoparticles will release from the solid phase to be collected as eluent following exit from the fluid conduit. In those embodiments in which the salt concentration is lowered over a period of time in a gradient fashion (e.g., multiple small steps or a continuous modification of the contents of the mobile phase), different components of the sample that may have adsorbed to the solid phase during the adsorption period can sequentially release from the solid phase to be separately eluted off of the column. Beneficially, due to the improved flow characteristics of the system incorporating the channeled fibers, this can provide a route to separating components that traditionally have been very difficult to separate from one another, e.g., different types of exosomes.

By way of examples, exosomes can elute off of a column at a different time point and at a different salt concentration than proteins of a sample; different exosome types can elute off of a column at different time points and different salt concentrations than each other; etc.

According to one embodiment, disclosed methods can be utilized in quantification of biologically active nanoparticles isolated according to the HIC process. Quantification methods can provide an approach for verification of desired separations among other benefits. In one embodiment, UV-vis absorbance can be used in quantifying and/or verifying separations of the system. For instance, a chromatogram can employ absorbance at about 216 nm in obtaining an indication of material exiting a column. 216 nm is a common wavelength used in protein chromatography, and fortuitously, many biologically active nanoparticles (e.g., exosomes) absorb at this wavelength as well. Thus, UV-vis absorbance appears to be a promising method of post-column quantification that could be useful for preparative purposes or future analytical assays. Additionally, one could easily envision multiple other detection methods including fluorescence and multi-angle light scatter (MALS), which would also provide size information of the eluting particles.

The HIC channeled fiber separation methods described herein can provide cheaper and more time-efficient methods for separation and isolation of biologically active nanoparticles. Not only can the disclosed platform be inexpensive (e.g., about $5 USD per column which can be used multiple times), but it can also be effective at isolation in a few minutes. Additionally, the versatility of the channeled fibers can allow for the addition of antibodies, surface chemistries, and other isolation modalities to transform a generic isolation protocol into a fast and effective type-specific separation method. Exclusive isolation of specific nanoparticles and reliable miRNA and particle surface marker protein interpretation capable by use of the disclosed methods may become an essential tool for medical diagnosis, and may prove especially useful for early diagnosis of diseases.

The present invention may be better understood with reference to the Example set forth below.

EXAMPLE

HIC exosome isolation methodology using channeled polymer fibers as stationary phase was compared to two commonly utilized exosome isolation methods including standard differential centrifugation (DC) (currently the most widely used isolation method), and the commercially available ExoEasy™ Maxi Kit (QIAGEN) (similar by virtue of its "chemical" separation approach). The utility of the disclosed separation method was further demonstrated by investigation of recovery of exosomes in mock urine and from cell culture media.

Exosome Expression by *Dictyostelium discoideum*

*D. discoideum* AX2 cells were grown and maintained axenically in HL5 medium supplemented with 100 μg $mL^{-1}$ ampicillin at room temperature in 25 $cm^2$ culture flasks. Cells were passaged at 70-90% confluency.

For exosome expression, AX2 cells were used to inoculate 50 mL of HL5 media supplemented with 100 μg/ml ampicillin at a starting cell concentration of $5\times10^5$-$10\times10^5$ cells $mL^{-1}$ in a 250 mL autoclaved Erlenmeyer flask (5 times the media volume for proper aeration) and supplemented with 100 μg $mL^{-1}$ ampicillin. After inoculation, the flask was covered in aluminum foil to block out light and placed on a shaker (150 RPM, 22° C.) for 48 hours.

Isolation of Exosomes Via Differential Centrifugation

Differential centrifugation (DC) was conducted as previously described by Tatischeff et al., with slight modifications. Briefly, all centrifugation steps performed below 12,000×g were performed using an Eppendorf Centrifuge 5430R (Eppendorf, Hamburg, Germany). Centrifugations of 12,000×g or more were performed using a Beckman Coulter Avanti J-26S XPI Centrifuge with a JA-25.50 rotor (Beckman Coulter, Brea, CA). The first centrifugation step was performed at 700×g (5 min., 22° C.) in a 50 mL conical centrifuge tube. After centrifugation, 45 mL of the supernatant was transferred to a new 50 mL conical centrifuge tube, with the remainder saved for exosome isolation via the disclosed HIC method. The second centrifugation was performed at 2,000×g (10 min., 22° C.) Following centrifugation, 40 mL of the supernatant was transferred to a sterilized 50 mL Nalgene centrifuge tube. The final centrifugation step was performed at 12,000×g (30 min., 4° C.) The supernatant was carefully removed and the final pellet was re-suspended in 400 μL of PBS and stored at 4° C.

Isolation of Exosomes Via Qiagen ExoEasy™ Maxi Kit

Exosome isolations were performed using a QIAGEN ExoEasy™ Maxi kit (QIAGEN, Hilden, Germany) per the manufacturer's instructions. All of the centrifugation steps required by the kit were performed using an Eppendorf Centrifuge 5430R (Eppendorf, Hamburg, Germany). Briefly, 10 mL of the *D. discoideum* cell growth media prepared for exosome isolation were filtered using a 0.8 μm syringe filter. An additional 1 mL of the remaining media was filtered using a 0.8 μm syringe filter and set aside for exosome isolation via the disclosed method. The resulting exosomes were eluted using 400 μL of the Qiagen XE elution buffer and stored at 4° C.

Hydrophobic Interaction Chromatography (HIC) Method Using Channeled Polymer Fibers Poly(ethylene terephthalate) (PET) channeled polymer fibers were obtained from the Materials Science and Engineering Department, Clemson University. All solvents were purchased from EMD (EMD Millipore, Billerica, MA). Ammonium sulfate ($(NH_4)_2SO_4$) and all other chemicals and proteins were purchased from Sigma-Aldrich (St. Louis, MO). Deionized water (DI-$H_2O$) was secured from a Milli-Q water system. The chromatographic exosome separations were performed on a Dionex Ultimate 3000 HPLC system, LPG-3400SD Quaternary pump, and MWD-3000 UV-vis absorbance detector (Thermo Fisher Scientific, Waltham, MA). A Rheodyne model 8125 low dispersion injector with 20 and 60 μL injection loops was used for exosome sample injections.

PET channeled fiber microbore columns (column length: 200 mm, i.d.: 0.762 mm) were used for the exosome separations, using lysozyme as the test protein. After flushing the column with buffer C (10 mM potassium phosphate buffer; pH=7.4), it was equilibrated with buffer A (1.8 M $(NH_4)_2SO_4$ solution dissolved in 1×PBS; pH=7.4). 30% acetonitrile (v/v) dissolved in 1×PBS was employed as buffer B. A mobile phase flow rate of 0.5 mL $min^{-1}$ and a 20 min gradient from 100% buffer A to 100% buffer B was used for exosome separation. Briefly, exosome samples were injected onto the column during the high-salt (buffer A) mobile phase. Under these conditions, latent proteins and exosomes were adsorbed to the PET fiber media, with the gradient subsequently eluting species of increasingly greater hydrophobicity. UV absorbance at 216 nm was monitored as a means of detecting the eluting species (proteins and exosomes). Based on the detector response reflecting their elution, purified exosomes were collected post-column.

HIC Elution and Isolation of Exosomes from Mock Urine and Cell Culture Media

Different amounts of previously isolated exosomes were spiked into a mock urine matrix (194 g urea, 6 g $CaCl_2$), 11 g $Mg_2SO_4$, and 80 g NaCl in 1 L of DI-$H_2O$), also containing added (spiked) myoglobin (Myo), α-chymotrypsinogen A (Chymo), ribonuclease A (Ribo) and lysozyme (Lyso) (0.1 mg $mL^{-1}$ each), as simple representatives of the variety of proteins present in urine. Subjection of these mixtures to the HIC protocol provided verification of isolation of the vesicles from the mock urine and quantification based on the integrated peak areas of the eluted exosomes. The gradient baseline absorbance representing the time frame of the exosome elution was obtained by running the gradient with no exosomes injected and was subtracted from the exosome-spiked separation chromatograms.

Exosome Population Characterization Via Nanoparticle Tracking Analysis (NTA)

NTA was performed using a Nanosight NS500 with a 532 nm laser and 565 nm long pass cut off fluorescent filter (Center for Nanotechnology in Drug Delivery, UNC Eshelman School of Pharmacy). Samples were diluted to a concentration between $1\times10^8$ and $5\times10^8$ particles $mL^{-1}$ with 20 nm filtered 1×PBS. For each sample, particles moving under Brownian motion were recorded on video five times for 40 seconds each. Hydrodynamic diameters were calculated using the Stokes-Einstein equation.

Scanning Electron Microscope Fixation and Imaging

The capture of intact exosomes from the various media onto the channeled polymer fiber surfaces was confirmed by scanning electron microscopy (SEM) imaging. PET channeled polymer fiber-packed tips were produced according to methods described previously. The fiber surfaces were wetted by flushing with 1 mL of $H_2O$, and then rinsed in 2M $(NH_4)_2SO_4$ in 1×PBS. 100 μL of each sample (DC-derived exosomes, culture milieu (HL5) or 2M $(NH_4)_2SO_4$) were mixed with 2M $(NH_4)_2SO_4$, followed by flushing through the tip (300×g for 5 min). The prepared fibers were fixed in 1% osmium tetroxide for 1 hour and washed 3 times for 3 minutes each in distilled water to remove any excess osmium tetroxide. Next, each sample was washed in a 6 step gradient of ethanol-distilled water solutions starting at 50% ethanol and ending at 100% ethanol for 3 minutes each. An additional 100% ethanol wash step was performed to ensure that all water had been removed from the sample. Finally, each sample was washed in a 50-50 Hexamethyldisilazane (HMDS)-ethanol solution for 3 minutes and left in 100% HMDS overnight. Samples were sputter-coated with platinum at 70 millitorr argon for 2 minutes using a Hummer 6.2 Sputtering system (Anatech USA, Union City, CA). SEM imaging was performed on a Hitachi S-4800 at 5.0 kV (Hitachi, Tokyo, Japan).

Results

Figure 6:
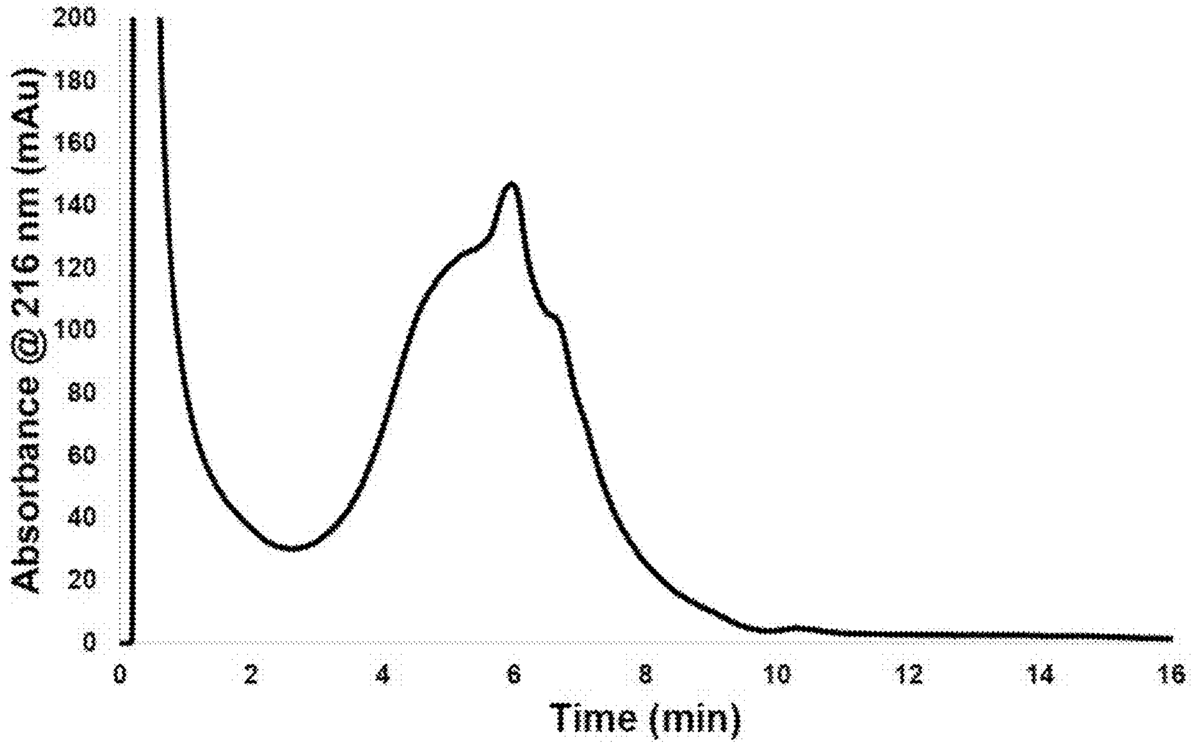
FIG. 6 presents a chromatogram obtained by the disclosed method showing the components of pristine culture media.
Figure 7:
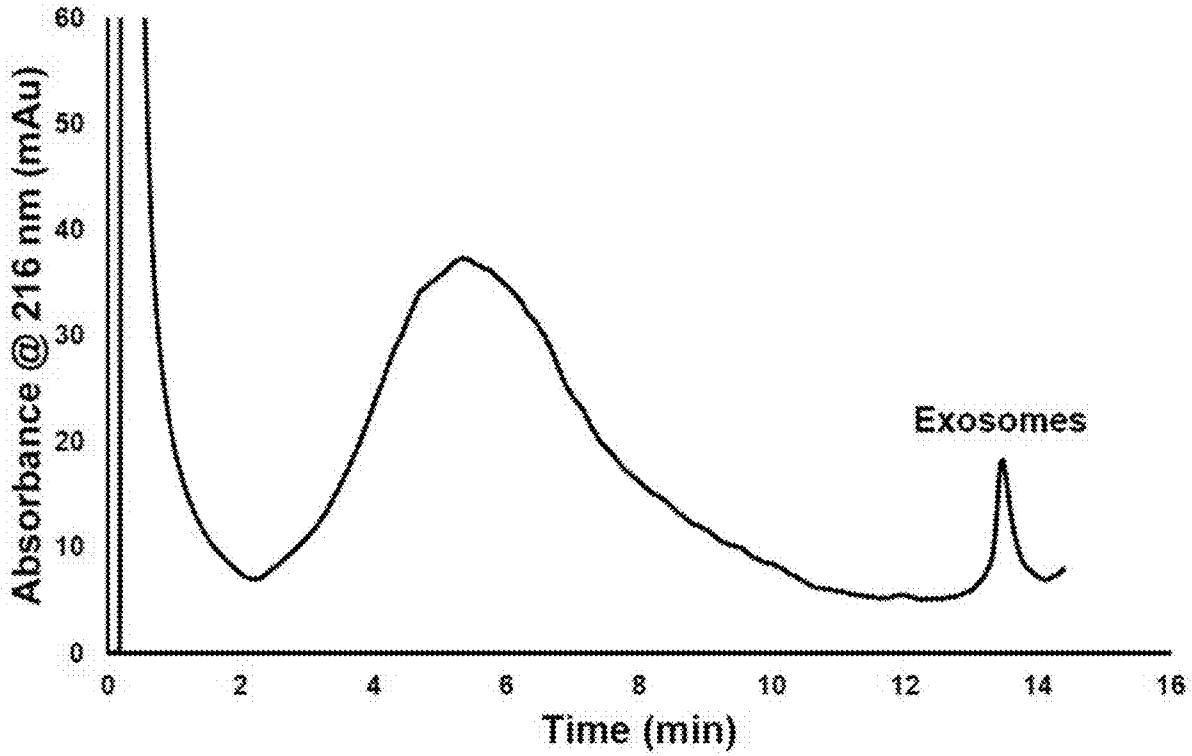
FIG. 7 presents a chromatogram obtained by the disclosed method showing isolation of *Dictyostelium discoideum*-derived exosomes previously isolated from the pristine media via differential centrifugation.
Figure 8:
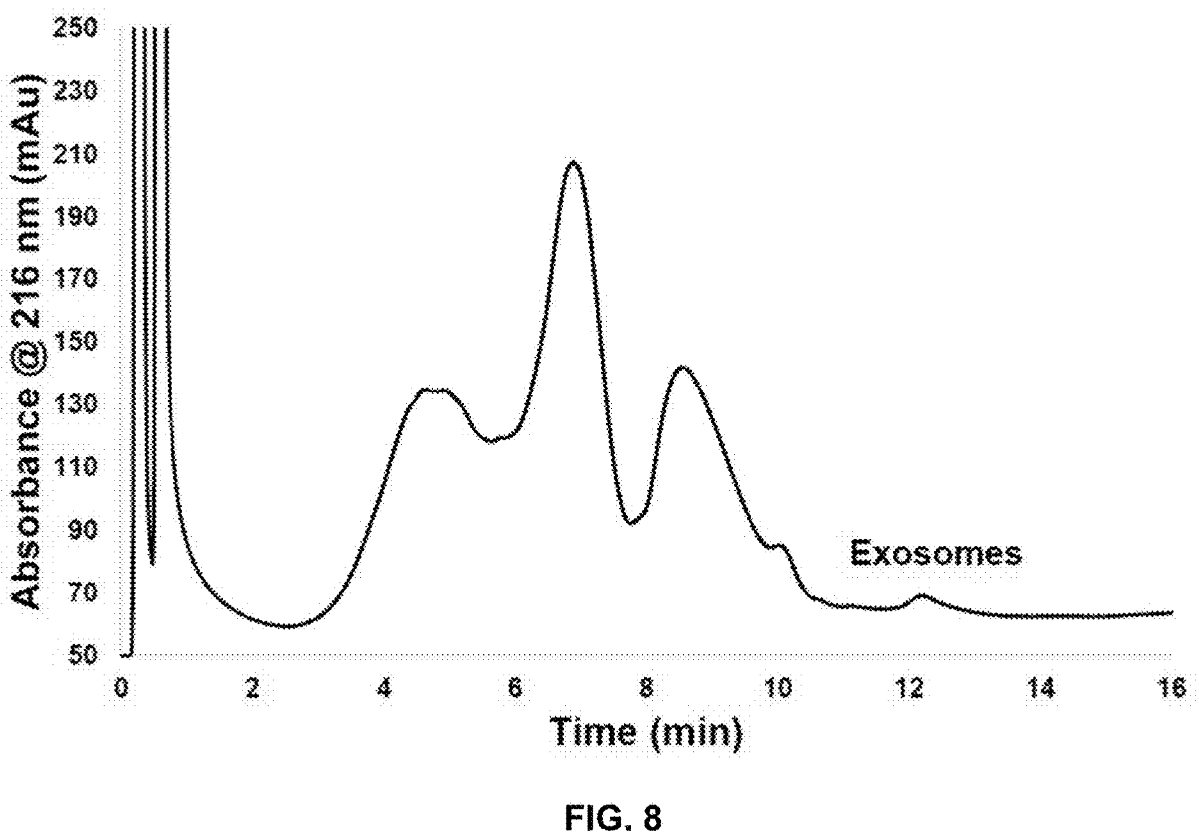
FIG. 8 presents a chromatogram obtained by the disclosed method showing isolation of *D. discoideum*-derived exosomes previously isolated from the pristine media via the Qiagen ExoEasy™ Maxi Kit.
Figure 9:
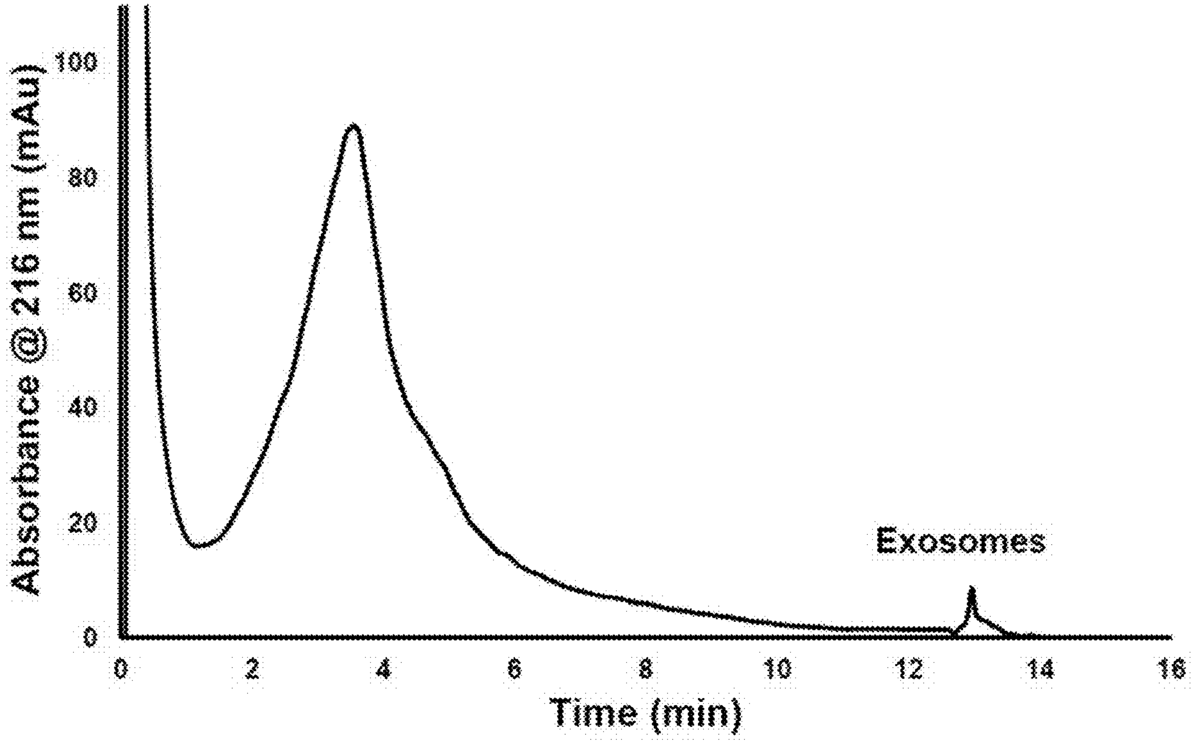
FIG. 9 presents a chromatogram obtained by the disclosed method showing isolation of *D. discoideum*-derived exosomes following centrifugation of the pristine media to remove cells and large debris.
Figure 10:
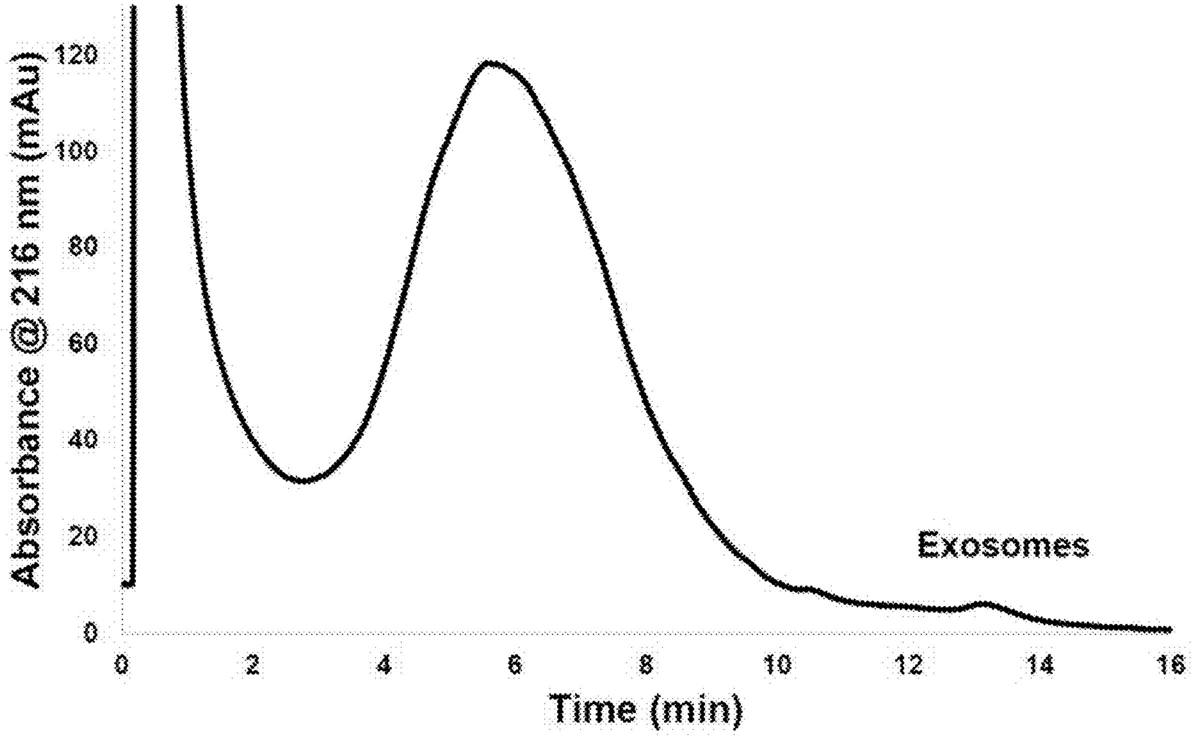
FIG. 10 presents a chromatogram obtained by the disclosed method showing isolation of *D. discoideum*-derived exosomes following filtration of the pristine media through a 0.8 μm filter to remove cells and large debris.

In order to determine whether or not exosomes could be isolated via HIC using the PET channeled fibers, the reserved aliquots of the *D. discoideum*-derived exosomes that had been previously isolated using the benchmark techniques were run on the PET channeled fiber columns with a mobile phase flow rate of 0.5 mL $min^{-1}$ and a 20 minute gradient from 100% buffer A to 100% buffer B. FIG. 6-FIG. 10 show the resulting chromatograms derived from pristine HL5 media and four different exosome isolation lots. In FIG. 6, results are shown for pristine HL5 injected onto a PET channeled fiber column for HIC analysis in order to establish a baseline chromatogram of the media components. The detector response shows a broadly eluting peak from approximately 2-10 minutes. This fraction is composed of media components including a myriad of proteins derived from yeast extract and peptone, various salts, and sugars. In FIG. 7, exosomes previously isolated via differential centrifugation were injected onto the fiber column for HIC analysis and separation. The resulting HIC chromatogram displays two major peaks, a very broad band between 2-11 minutes, and a fairly sharp feature reflecting a more strongly retained (hydrophobic) species with an elution time of ~13-13.5 mins along the 20 minute gradient. In FIG. 8, exosomes previously isolated via the ExoEasy™ kit were injected onto a PET channeled fiber column for HIC analysis and separation. The resulting HIC chromatogram displays four major peaks. In this case, the first three peaks are better-resolved than the first, broad peaks in FIGS. 6 and 7, but, taken as a group, still elute within the same time frame of 2-11 minutes. Once again, as in FIG. 7, a fairly sharp feature reflecting a more strongly retained (hydrophobic) species with an elution time of ~13-13.5 min is seen. Based on the structure of the respective chromatograms, it is not unreasonable to suggest that the peaks eluting between 2-11 minutes represent remaining HL5 media components as well as host cell (*D. discoideum*) proteinaceous and genetic material, salts, and other small molecules left behind during the previous isolation procedures, with the later eluting (13-13.5 min) smaller, sharper peaks representing exosomes. Further confirmation is presented in particle tracking data and SEM images discussed herein.

These results strongly suggest that the disclosed HIC method is effective at separating the population of exosomes from other chemical species inherent in the spent cell media. Indeed, the presence of the broad concomitant elution bands reflects the non-specificity that exists in the DC and ExoEasy™ methods. The resulting exosome peak is very clean and it is easy to separate the exosomes from the other species due to its unique elution time. The eluted exosome fractions from these isolations were collected and saved for NTA analysis. It is also interesting to note that, based on the absorbance scales, there is far greater protein carryover in the ExoEasy™ isolation method, which is not surprising given the nature of the solid phase employed in that process versus a DC procedure.

In order to more realistically compare the efficiencies of the channeled polymer fiber HIC method with the benchmark methods, *D. discoideum* cell cultures were processed in similar fashions in terms of removing whole cells and cellular debris. In the case of DC, simple centrifugation was the first step. For comparison to the ExoEasy™ Kit, filtration was employed to clear the macroscale debris. The resulting culture milieu solutions, having the exosomes in their native (relatively dilute) concentrations, were then subjected to HIC using the PET channeled fibers using the same gradient conditions as the DC- and ExoEasy™-isolated separations.

The chromatogram of the centrifuged *D. discoideum* cell culture milieu (FIG. 9), displays two prominent peaks that appear at elution times of 2-11 and approximately 13 minutes, respectively. Once again, a broader peak, likely representing various media components and cellular metabolites and debris, is seen as in FIGS. 6 and 7. A smaller second peak is also seen that, as before, is a more discrete population of more hydrophobic species that is likely exosomes. The relative responses for the concomitant species and the exosomes make sense as there is apt to be more debris and proteinaceous material, and lower exosome concentrations, in the milieu sample than in the sample of exosomes previously isolated via differential centrifugation and re-suspended in 1×PBS. In addition, the exosome peak from the milieu is smaller, as the exosome concentration in the milieu is much more dilute than the re-suspended exosome samples.

The corresponding HIC chromatogram taken of the filtered cell culture media (FIG. 10) also shows a pronounced, broad peak at early elution times, with a relatively small peak in the window corresponding to exosome elution. In comparison to the centrifuged milieu (FIG. 9), the exosome fraction is much smaller than the concomitants. On the surface, this would seem to indicate that there is exosome loss in the filtration process, which is not unreasonable as the filter material itself is composed of both hydrophobic and hydrophilic layers. It is interesting to note that the same relationship appears when comparing the DC- and ExoEasy™-isolated exosome chromatograms (FIGS. 7 and 8) where those two primary cleanup processes are employed.

Comparison of Exosome Recoveries for the Different Isolation Methodologies

NTA is a widely-accepted method for the evaluation of exosome concentration and size distribution. As such, NTA was used to measure these parameters for the initial exosome isolations from both the DC and ExoEasy™ kit procedures, as well as the concentration of the exosome fractions from the HIC isolations. FIG. 11 provides an overview of the procedural steps and exosome concentration results for each exosome isolation protocol. All values were normalized to number of particles (exosomes) derived from 50 mL of the starting cell culture. Reported values are averages from triplicate isolations. The protocol of Column a includes Exosomes isolated via differential centrifugation. Column b—exosomes isolated via Qiagen ExoEasy™ Maxi Kit. Column c—exosomes first isolated via differential centrifugation and re-suspended in 400 μL 1×PBS, followed by subsequent re-isolation of exosomes via PET channeled fiber HIC. Column d—exosomes first isolated via differential centrifugation and re-suspended in 400 μL Qiagen elution buffer, followed by subsequent re-isolation of exosomes via PET channeled fiber HIC. Column e—cell culture media cleared of cells and large debris via centrifugation, followed by exosome isolation via PET channeled fiber HIC. Column f—cell culture media cleared of cells and large debris via filtration, followed by exosome isolation via PET channeled fiber HIC.

Due to the fact that all of the particles counted during the NTA may not be exosomes (protein aggregates and other cellular debris would also be counted), the resulting values (presented as particles-per-mL) given in FIG. 11, should be evaluated and compared to one another based on their order of magnitude values as opposed to their discrete values. When compared in this manner, it can be seen that the differential centrifugation (column a) and ExoEasy™ kit (column b) yield comparable exosome/particle recoveries. FIG. 11 also shows that the PET channeled fiber HIC exosome isolation method, regardless of whether the cell culture was first centrifuged (column e) or filtered (column f) to remove cells and large debris, yielded the same order of magnitude values as either benchmark method alone. This demonstrated that the ability of the channeled fiber HIC isolation method to effectively isolate exosomes is on par with the two benchmark isolation methodologies examined in this study.

While the concentration results for all of the single isolation trials (FIG. 11, columns a, b, e, f) were of the same order of magnitude, it should be noted that the results from the HIC processing of the re-suspended exosomes originally isolated via differential centrifugation (column c) or the ExoEasy™ kit (column d) were lower by approximately two orders of magnitude. Several factors may be responsible for the lower than expected exosome concentrations seen following the secondary PET channeled fiber HIC isolation. First, both differential centrifugation and the ExoEasy™ Maxi kit utilize high-speed centrifugation steps that can potentially lead to vesicle disruption or aggregation. In addition, due to the size of the parallel channels of the channeled fibers, large aggregates of exosomes may become trapped on the fibers and unable to elute. Likewise, large exosome aggregates may experience enhanced surface adhesion causing a large portion of exosomes to not elute from the column, i.e., irreversible binding. At high concentrations, exosomes have a tendency to precipitate out of solution and aggregate over time. Finally, the respective isolate solvents in DC and ExoEasy™ may lead to decreased adsorption/capture of the exosomes on the PET fiber surfaces. Therefore, the actual concentration of exosomes in the liquid phase of the initial exosome aliquots used for injection onto the channeled fiber columns for subsequent HIC separation may have been lower than the initial exosome concentrations as measured in the aliquot sent for NTA analysis.

The particle size distributions, as measured by NTA, were also very similar across all of the isolated exosome samples, regardless of the isolation method (Table 1, below). The resultant NTA size distribution graphs from all of the exosome samples contained a prominent high concentration peak on the lower range of the size distribution scale ranging from about 90 to about 160 nm, typically representing about 70% of the total population (NTA graphs not shown). Further examination of the NTA results revealed that all of the exosome samples had similar size distributions to the *D. discoideum* exosome NTA size distributions as previously reported.

TABLE 1

| Exosome Isolation Method | Mean (nm) | Mode (nm) | Standard Deviation (nm) | $10^{th}$ Percentile (nm) | $90^{th}$ Percentile (nm) |
|---|---|---|---|---|---|
| DC | 183 | 143 | 66.3 | 119 | 257 |
| DC + HIC | 192 | 143 | 89.6 | 103 | 303 |
| ExoEasy ™ | 154 | 97.1 | 80.2 | 87.6 | 63 |
| ExoEasy ™ + HIC | 161 | 128 | 55.9 | 92.9 | 223 |
| Centrifuge + HIC | 155 | 121 | 60.1 | 106 | 228 |
| Filtered + HIC | 142 | 108 | 60.4 | 87.6 | 206 |

Most of the NTA size distributions contained additional populations of lower concentration at larger sizes. This is most notable in the samples isolated via differential centrifugation (Table 1), which happen to demonstrate a slightly higher overall average particle size than the samples isolated by the other methodologies. The uniformity of the distributions across all of the isolation methods suggests that the additional lower concentration peaks at larger sizes may be due to aggregated exosomes. In addition, larger, non-exosome particles and protein aggregates could also contribute to these populations. This makes sense as differential centrifugation is known to cause both exosome and protein aggregation to a greater extent than other isolation methods. If exosome or protein aggregates are present, these could be due to the isolation process used or as a result of the conditions of the sampling, packaging, and shipping of the materials for NTA characterization. Collectively, the NTA results demonstrate that the channeled fiber HIC exosome isolation method is as effective as the benchmark isolation methods.

FIG. 11 also presents the time required for each of the isolation processes to be completed. Differential centrifugation was the most time consuming method, requiring more than 2 hours to perform (columns a, c). In comparison, the ExoEasy™ kit required approximately 30 minutes (columns b, d), while the HIC method can be affected in only 8 minutes (columns e, f).

Imaging

Figure 12:
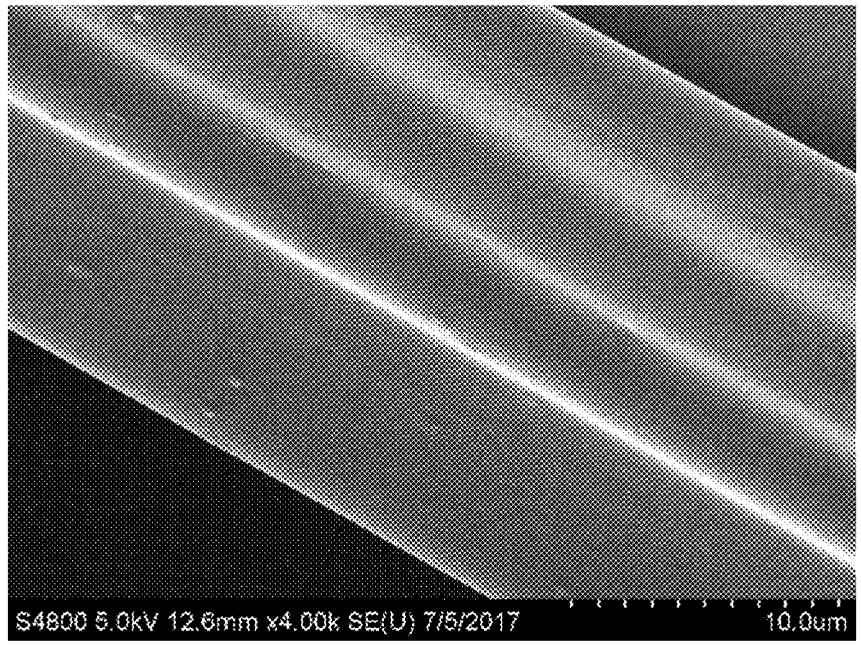
FIG. 12 presents a scanning electron microscope (SEM) image of PET channeled fibers exposed to a 2M ammonium sulfate control.
Figure 13:
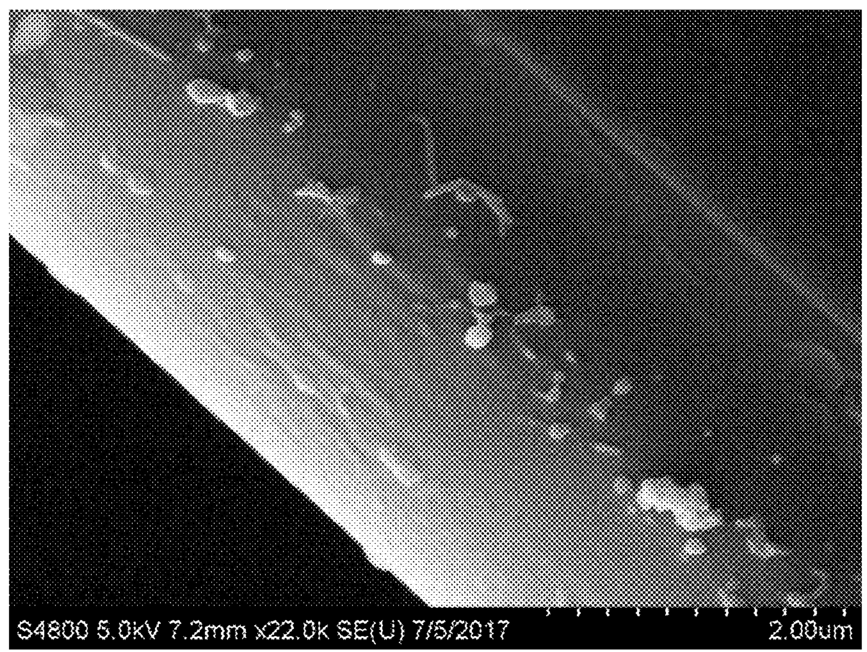
FIG. 13 presents an SEM image of *D. discoideum*-derived exosomes isolated on a PET channeled fiber via HIC, the exosomes were previously isolated via differential centrifugation.
Figure 14:
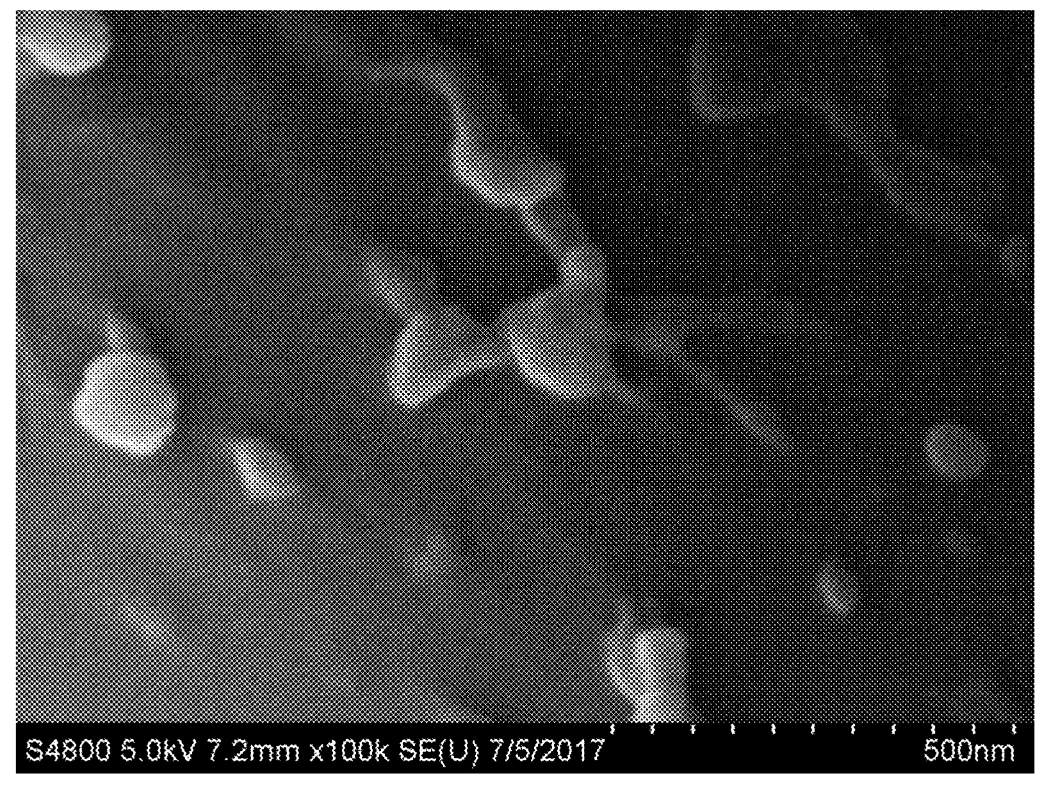
FIG. 14 provides a higher magnification image of exosomes depicted in FIG. 13, showing detail of exosome interactions with each other and the fiber surface.

Scanning electron microscope (SEM) images were collected to visually verify the presence of exosomes and to investigate how they physically interact with the channels of the fibers prior to elution. Exosomes that had been isolated from *D. discoideum* cell culture media via differential centrifugation and re-suspended in 1×PBS and *D. discoideum* cell culture milieu were added to the 2M ammonium sulfate chromatographic mobile phase and then each spun through PET channeled fiber micropipette tips using a solid phase extraction technique. In addition, 2M ammonium sulfate was spun through a separate tip as a non-exosome control. In both cases, an aqueous wash step was employed following exposure to remove any accumulated media particulates. As seen in FIG. 12, the fibers exposed only to the salt media show a very smooth surface, with multiple channels of the same fiber seen at this 10.0 μm-scaled micrograph. Passage of the DC-derived media through the fibers shows clearly the adsorption of vesicle material (FIG. 13, 14). As seen in FIG. 13 (2.0 μm-scale), there are a large number of vesicles, most as individual entities, but some appearing as aggregates. It could not be confirmed whether or not the agglomerates were formed on the fiber surface or originated in the milieu. Further magnification of the DC-derived aliquot (FIG. 14, 500 nm scale) provides detail of individual exosomes on the PET fiber surfaces with some neighboring exosomes touching one another and even stretching or elongating as they adhere to the fiber.

While the SEM imaging demonstrates the phenomenon of the immobilization of the hydrophobic exosomes on the fiber surfaces, it also suggests that the fiber platform might be a valuable means of studying exosome agglomeration or other physical or biological phenomena. Likewise is shows that further chemistries might be applied to the surface adsorbed exosomes to better affect detection and/or use lysing means to rupture the exosomes to then collect their content.

Figure 15:
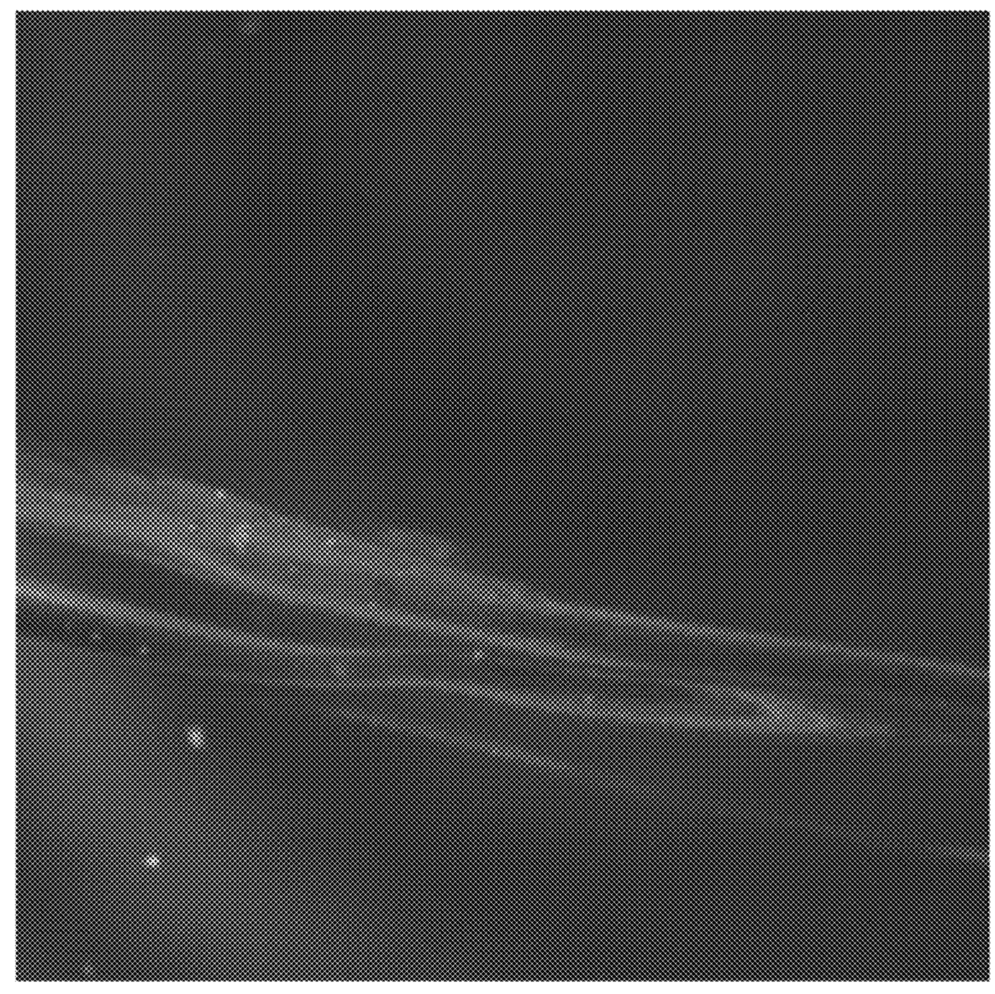
FIG. 15 is a confocal microscopy image of fiber-captured exosomes derived from CaOv-3 ovarian cancer. The cancer cells were identified with a primary antibody to the CA125 surface protein and an AlexaFluor 488-labeled secondary antibody. The image was taken using super-resolution confocal laser scanning microscopy (CLSM).

As an example of application of chemistries such as detectable labels to adsorbed exosomes, FIG. 15 provides a confocal microscopy image of fiber-captured exosomes derived from CaOv-3 ovarian cancer cells and identified via a primary antibody to the CA125 surface protein for initial capture of the exosomes followed by detection by use of an AlexaFluor 488-labeled secondary antibody. Following application of the detectable label to the previously adsorbed exosomes, the labeled exosomes were imaged by super-resolution confocal laser scanning microscopy. This demonstrates the concept of confirming the presence of cell-specific exosomes, as might be applied in a clinical diagnostic protocol.

Isolation of Exosomes Via HIC from a Mock Urine Matrix

Exosomes that had been previously isolated via differential centrifugation were spiked into a mock urine matrix containing model proteins (myoglobin (Myo), α-chymotrypsinogen A (Chymo), ribonuclease A (Ribo), and lysozyme (Lyso)), each at a concentration of 0.1 mg $mL^{-1}$. In this way, isolation from both urine matrix components and concomitant proteins was demonstrated using the same gradient as employed in the separations described above.

Figure 16:
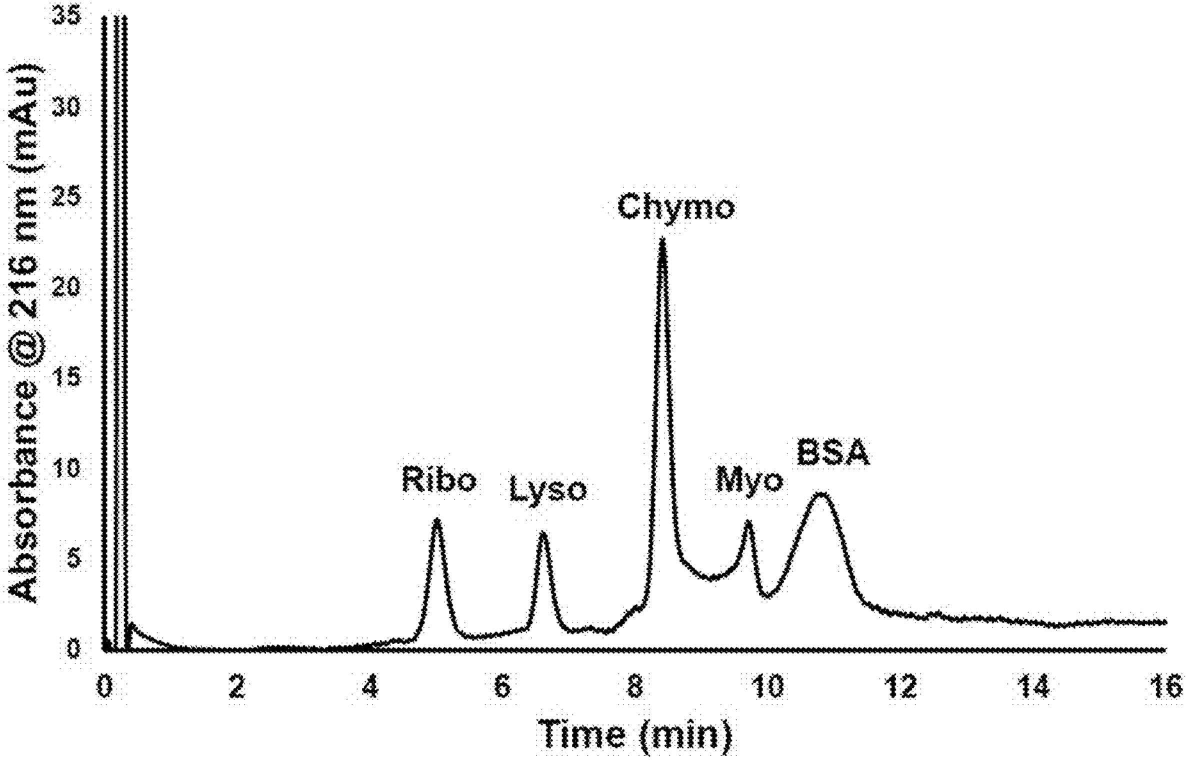
FIG. 16 provides a PET channeled fiber HIC chromatogram of mock urine matrix spiked at 0.1 mg ml$^{-1}$ concentration with model proteins.
Figure 17:
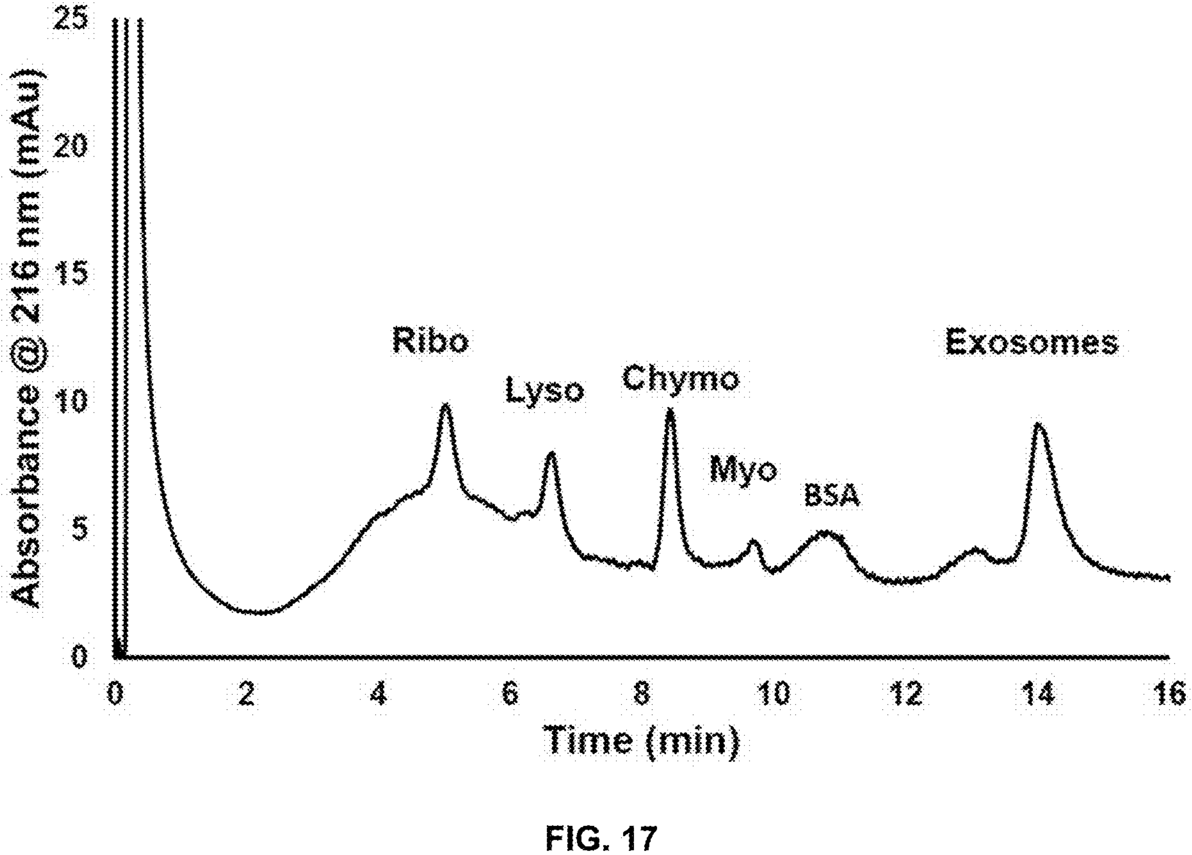
FIG. 17 provides a PET channeled fiber HIC chromatogram of a 50:50 mixture of mock urine and DC-isolated exosomes.

FIG. 16 shows the HIC chromatogram of the mock urine matrix, which established baseline elution times for the individual matrix components. As shown, the five spiked proteins were very well resolved, with the other matrix species eluting as a band over the 8-10 min elution window. As seen in FIG. 17, when the mock urine was spiked 50:50 with DC-isolated exosomes and subsequently run on the HIC columns, the chromatogram revealed the expected peaks from the spiked proteins along with an additional, later-eluting prominent peak attributed to the exosomes. Interestingly, the added proteins appear as discrete peaks superimposed on a broader peak believed to be remnant proteins and debris associated with the spiked exosomes following their isolation via DC as presented in FIG. 17.

Exosome Quantification

Figure 18:
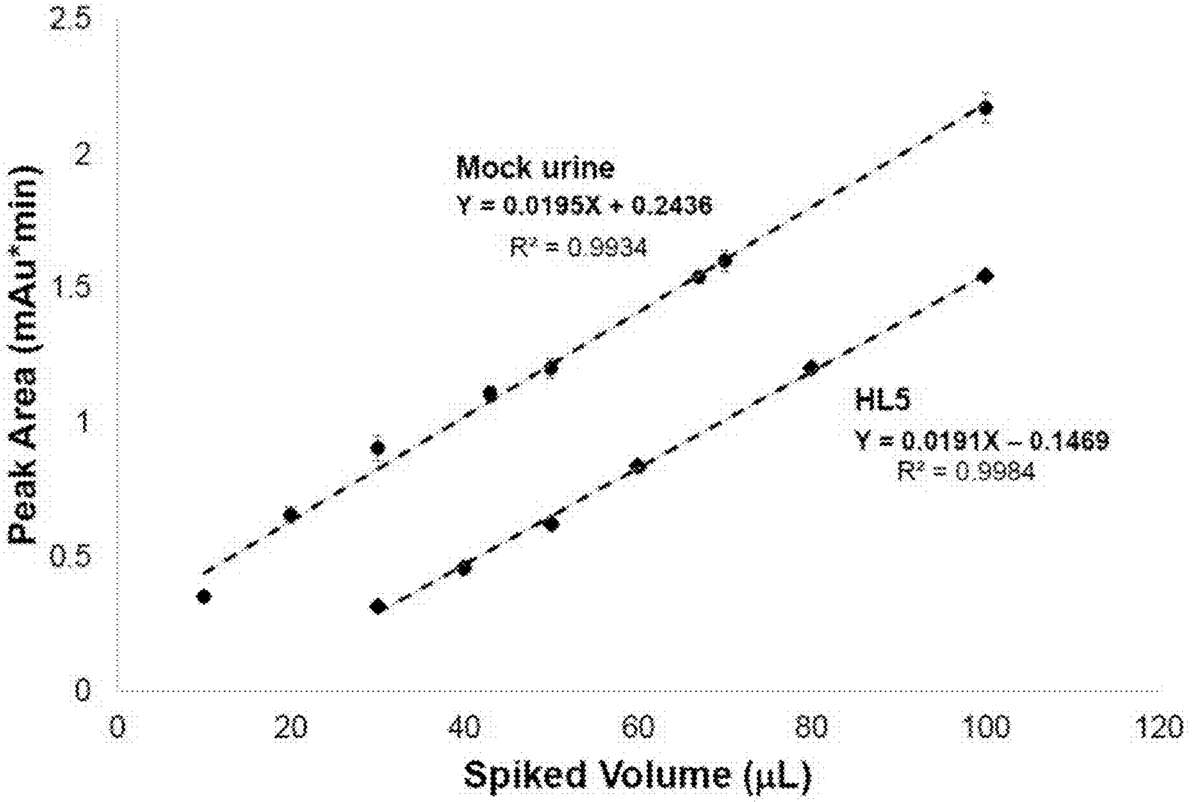
FIG. 18 presents analytical response curves for separations of different samples according to disclosed methods.

To establish whether or not a relationship existed between exosome concentration and absorbance, increasingly larger aliquots of exosomes, previously isolated via DC, were added to 100 μL aliquots of the mock urine and culture milieu (HL5) matrices and the integrated absorbance values for the peaks eluting between 13-14 minutes were recorded. As shown in FIG. 18, a direct proportionality did indeed exist, reflecting a quantitative recovery of exosomes from the HIC channeled fiber separation method. As shown, the slopes of the two response curves were virtually identical, implying that the purity of the isolated fractions was very consistent between the two matrix forms. It was not possible to place firm concentration values on the results of these experiments, as a certified reference material does not exist. Based on the NTA values presented in Table 1 for the DC method, the working range presented in FIG. 17 is approximately 0.1-7×$10^9$ particles for the 20 μL injections employed here. Based on the presented response functions, it is not difficult to imagine limits of detection for this simple method to be approximately 5×$10^7$ particles.

Figure 19:
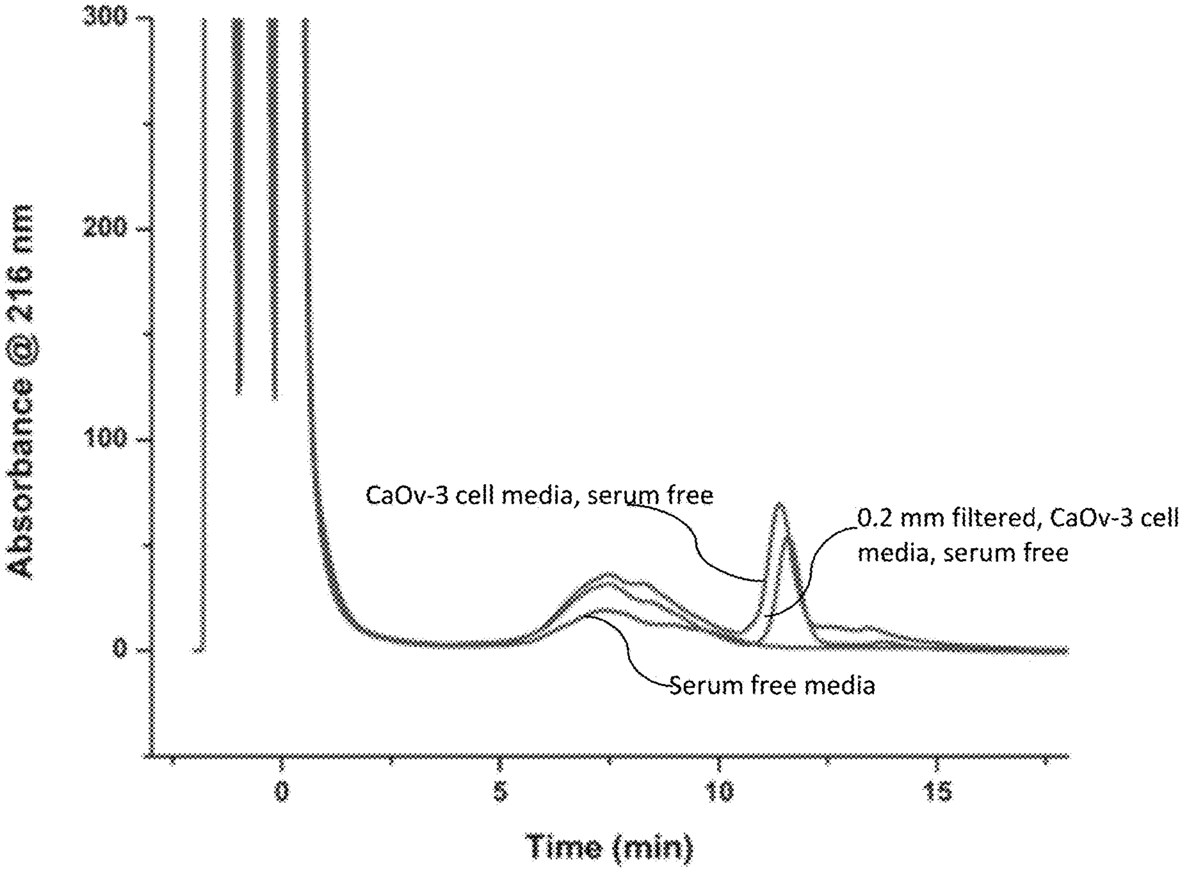
FIG. 19 provides PET channeled fiber HIC chromatograms comparing serum free media, exosomes produced by CaOv-3 ovarian cancer cells grown in serum free media, inclusive of direct supernate injection and supernate subjected to 0.2 mm filtration.

These results indicate that the channeled fiber HIC columns may be utilized to isolate exosomes directly from biological samples such as urine. The method can also be extended to cells grown in various media. For instance, FIG. 19 provides PET channeled fiber HIC chromatograms of exosomes produced by CaOv-3 ovarian cancer cells grown in serum free media, inclusive of direct supernate injection and supernate subjected to 0.2 mm filtration.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for separating biologically active nanoparticles from a mixture comprising:

flowing a mobile phase through a fluid conduit, the mobile phase including a sulfate salt at a first concentration, the sulfate salt is ammonium sulfate or sodium sulfate, the fluid conduit containing a polymeric stationary phase that defines a plurality of passages through the fluid conduit, the passages defining a cross sectional dimension of from about 1 micrometer to about 4 micrometers, the polymeric stationary phase comprises a polymer, wherein the polymer is selected from the group consisting of polyvinyl alcohol, nylon, polysulfone, polymethyl methacrylate, polyethylene terephthalate, polyepoxies, polvinylidone chloride, acrylonitrile butadiene styrene, polycarbonate, and polyvinyl chloride, and wherein the polymeric stationary phase having a critical surface tension of about 35 $mJ/m^2$ or greater and a water contact angle of about 85° or less;

combining a mixture with the mobile phase, the mixture comprising biologically active nanoparticles, free proteins, and other matrix species, the biologically active nanoparticles comprising an envelope that includes a lipid bilayer, wherein upon the combination and at the first concentration of the sulfate salt, the biologically active nanoparticles and the free proteins adsorb or bind to the surface of the stationary phase as the mobile phase flows though the fluid conduit;

adding an organic modifier or a surfactant to the mobile phase following the adsorption or binding of the biologically active nanoparticles and the free proteins;

decreasing the first concentration of the sulfate salt in the mobile phase to a second concentration of the sulfate salt following the addition of the organic modifier or surfactant, at which second concentration the free proteins elute off of the surface of the stationary phase and the biologically active nanoparticles remain adsorbed or bound to the surface of the stationary phase; and further decreasing the second concentration of the sulfate salt in the mobile phase to a third concentration of the sulfate salt, at which third concentration the biologically active nanoparticles elute off of the surface of the stationary phase.

2. The method of claim 1, further comprising binding a detectable label to the biologically active nanoparticles.

3. The method of claim 1, further comprising following the adsorption or binding, lysing the biologically active nanoparticles.

4. The method of claim 1, the polymeric stationary phase comprising a fiber that defines a plurality of co-linear channels, the hydrophobic surface including a surface of the co-linear channels.

5. The method of claim 1, the polymeric stationary phase comprising a polymer selected from the group consisting of a polyvinyl alcohol, a nylon, a polymethyl methacrylate, a polyethylene terephthalate, a polyepoxy, a polyvinylidone chloride, and an acrylonitrile butadiene styrene.

6. The method of claim 1, wherein the biologically active nanoparticles comprise natural nanoparticles.

7. The method of claim 1, wherein the biologically active nanoparticles comprise exosomes.

8. The method of claim 1, wherein the decrease from the first concentration of the sulfate salt to the second concentration of the sulfate salt is a gradual decrease and/or wherein the decrease from the second concentration of the sulfate salt to the third concentration of the sulfate salt is a gradual decrease.

9. The method of claim 1, wherein the mixture is derived from a biological source, or the mixture comprises a biological fluid, or the mixture comprises cell culture media.

10. The method of claim 1, wherein the conduit exhibits a backing pressure of about 500 psi to about 1000 psi at a mobile phase flow rate of about 0.5 mL/min to about 3 mL/min through the conduit.

11. The method of claim 1, wherein the first concentration of the sulfate salt is from about 1 M to about 3 M.

12. The method of claim 1, the mobile phase having a linear velocity through the conduit of about 50 mm/second or greater.

13. The method of claim 1, wherein the stationary phase comprises a bundle of aligned fibers, or wherein the stationary phase consists of a single fiber, or wherein the stationary phase comprises a flat fiber or film including a plurality of channels linearly adjacent to one another.

14. The method of claim 1, further comprising imaging the biologically active nanoparticles when they are adsorbed or bonded to the surface of the stationary phase.

15. The method of claim 1, wherein the fluid conduit is a spin-down column.

16. The method of claim 1, wherein the organic modifier is selected from the group consisting of acetonitrile, an alcohol, a polyol, and combination thereof.

17. The method of claim 16, wherein the organic modifier comprises glycerol.

18. The method of claim 1, wherein the surfactant is sodium dodecylsulfate, polyethylene glycol tert-octylphenyl ether, or cetyltrimethylammonium bromide.

19. The method of claim 1, wherein the biologically active nanoparticles are selected from the group consisting of virus, bacteria, whole cells, lysosomes, liposomes, and vacuoles.

20. The method of claim 1, wherein the biologically active nanoparticles are synthetic biologically active nanoparticles.

21. The method of claim 1, wherein the step of separating biologically active nanoparticles from a mixture is after a step of pretreatment.

22. The method of claim 1, wherein the step of separating biologically active nanoparticles from a mixture is after a step of filtration.

* * * * *